US012699080B2

(12) United States Patent
    Rabenhorst

(10) Patent No.: US 12,699,080 B2
(45) Date of Patent: Aug. 4, 2026

(54) SYSTEMS, METHODS AND INDICATOR MATERIALS FOR ASSESSING REDUCTION STATE IN SOILS

(71) Applicant: University of Maryland, College Park, College Park, MD (US)

(72) Inventor: Martin C. Rabenhorst, University Park, MD (US)

(73) Assignee: University of Maryland, College Park, College Park, MD (US)

( * ) Notice: Subject to any disclaimer, the term of this patent is extended or adjusted under 35 U.S.C. 154(b) by 352 days.

(21) Appl. No.: 18/297,731

(22) Filed: Apr. 10, 2023

(65) Prior Publication Data

US 2023/0314398 A1      Oct. 5, 2023

Related U.S. Application Data

(63) Continuation of application No. 16/340,274, filed as application No. PCT/US2017/059076 on Oct. 30, 2017, now Pat. No. 11,656,215.

(Continued)

(51) Int. Cl.
    *G01N 33/24*          (2006.01)
    *B01L 3/00*           (2006.01)
    (Continued)

(52) U.S. Cl.
    CPC ............ *G01N 33/24* (2013.01); *B01L 3/5082* (2013.01); *C01G 45/02* (2013.01); *G01N 1/08* (2013.01);
    (Continued)

(58) Field of Classification Search
    CPC .......... G01N 33/24; G01N 1/08; G01N 31/22; G01N 33/00; G01N 2001/021;
    (Continued)

(56) References Cited

U.S. PATENT DOCUMENTS

| | | | |
|---|---|---|---|
| 5,070,597 | A | 12/1991 | Holt et al. |
| 5,224,373 | A | 7/1993 | Williams et al. |

(Continued)

FOREIGN PATENT DOCUMENTS

| | | | | |
|---|---|---|---|---|
| CN | 100342063 | | 10/2007 | |
| CN | 104355334 A | * | 2/2015 | ......... C08G 73/0611 |

(Continued)

OTHER PUBLICATIONS

DE102012005015A1 Translation merged with original (Year: 2013).*

(Continued)

*Primary Examiner* — Pamela H Weiss
(74) *Attorney, Agent, or Firm* — HYLTON-RODIC LAW PLLC

(57)          ABSTRACT

The present invention relates an indicator system for assessing a reduction state of unconsolidated material that includes a delivery tube defining an interior chamber, and a substrate disposed within the interior chamber and including a reactive coating thereon. The reactive coating is at least partially removable from the substrate upon exposure to a reducing condition of unconsolidated material over a period of time. An indicator device including a reactive coating comprising a manganese oxide is also disclosed.

4 Claims, 17 Drawing Sheets

Related U.S. Application Data

(60) Provisional application No. 62/517,628, filed on Jun. 9, 2017, provisional application No. 62/414,853, filed on Oct. 31, 2016.

(51) Int. Cl.

| | |
|---|---|
| *C01G 45/02* | (2025.01) |
| *G01N 1/02* | (2006.01) |
| *G01N 1/08* | (2006.01) |
| *G01N 31/22* | (2006.01) |
| *G01N 33/00* | (2006.01) |

(52) U.S. Cl.
CPC ............. *G01N 31/22* (2013.01); *G01N 33/00* (2013.01); *B01L 2200/025* (2013.01); *B01L 2200/12* (2013.01); *B01L 2300/0832* (2013.01); *B01L 2300/123* (2013.01); *C01P 2002/72* (2013.01); *G01N 2001/021* (2013.01)

(58) Field of Classification Search
CPC ............. B01L 3/5082; B01L 2200/025; B01L 2200/12; B01L 2300/0832; B01L 2300/123; C01G 45/02; C01P 2002/72
See application file for complete search history.

(56) References Cited

U.S. PATENT DOCUMENTS

| | | | | |
|---|---|---|---|---|
| 6,214,088 | B1 | 4/2001 | Karamanev | |
| 6,488,890 | B1 | 12/2002 | Kirckof | |
| 6,514,765 | B1 | 2/2003 | Scaringe et al. | |
| 6,766,762 | B2 | 7/2004 | Jenkinson et al. | |
| 7,550,297 | B2 | 6/2009 | Rabenhorst | |
| 11,656,215 | B2 * | 5/2023 | Rabenhorst | G01N 1/08 436/28 |
| 2005/0287682 | A1 | 12/2005 | Lizzi | |
| 2007/0009809 | A1 * | 1/2007 | Krekeler | A01G 24/15 430/5 |
| 2008/0138910 | A1 | 6/2008 | Guga | |
| 2008/0199363 | A1 | 8/2008 | Mao | |
| 2010/0112680 | A1 | 5/2010 | Brockwell | |
| 2011/0142748 | A1 * | 6/2011 | Lambert | C01G 45/1228 423/579 |
| 2014/0209392 | A1 * | 7/2014 | Jamison | C09K 8/032 175/217 |
| 2015/0315068 | A1 * | 11/2015 | Clatot | C03B 5/027 65/29.21 |
| 2019/0285607 | A1 * | 9/2019 | Rabenhorst | G01N 31/22 |

FOREIGN PATENT DOCUMENTS

| | | | | | |
|---|---|---|---|---|---|
| DE | 10/2012/005015 | | 9/2013 | | |
| DE | 102012005015 | A1 * | 9/2013 | ........ | C01G 45/1221 |
| JP | 2011207725 | A * | 10/2011 | | |
| JP | 5598844 | B2 * | 10/2014 | | |
| WO | WO 2012/113032 | | 8/2012 | | |
| WO | WO 2016/059988 | | 4/2016 | | |

OTHER PUBLICATIONS

A simple method to synthesize birnessite at ambient pressure and temperature Matthias Handle Thilo Rennert Kai Totsche Geoderma 193-194 (2013) 117-121 (Year: 2013).*
Synthesis and Delmination of Layered Manganes Oxide Nanobelts Zhaoping Liu Renzhi Ma Yasuo Ebina Kazunori Takada and Takayoshi Sasaki Chem Mater 2007 19 65046512 (Year: 2007).*
A Simple Method to Syntheszie Birnessite at Ambient Pressure and Temperatuer Matthias Handel Thilo Rennert Kai U Totsche Geoderma 193-194 2013 117-121 (Year: 2013).*
Bohn, H.L. (1971) "*Redox Potentials*," Soil Science 112:39-45.

Castenson, K. et al. (2006) "*Indicator of Reduction in Soil (IRIS): Evaluation of a New Approach for Assessing Reduced Conditions in Soil*," Soil Sci. Soc. Am. J. 70:1222-1226.
Childs, C.W. (1981) "*Field Tests for Ferrous Iron and Ferric-organic Complexes (on Exchange Sites or in Water-soluble Forms) in Soils*," Aust. J. Soil Res. 19:175-180.
Coffin, C.A. (2012) "*Indicators of Reduction in Soils (IRIS) in Various Conditions of Saturation in South Florida MARL*," M.S. thesis. Univ. of Florida, Gainesville (46 pages).
Dorau, K. et al. (2016) "*Comparison of Manganese and Iron Oxide-coated Redox Bars for Characterization of the Redox Status in Wetland Soils*," Wetlands 36:133-141.
Dorau, K. et al. (2015) "*Manganese and Iron Oxide-Coated Redox Bars as a Tool to In-Situ Study the Element Sorpotion in Wet Soils*," J. Soils Sediments 16:976-986.
Dorau, K. et al. (2015) "*Manganese-Oxide-Coated Redox Bars as an Indicator of Reducing Conditions in Soils*," J. Environ. Qual. 44:696-703.
Dorau, K. et al. (2015) "*Manganese-Oxide-Coated Redox Bars as an Indicator of Reducing Conditions in Soils*," J. Environ. Qual. 44:696-703 Supplemental Material 5 pages.
Handel, M. et al. (2013) "*A Simple Method to Synthesize Birnessite at Ambient Pressure and Temperature*," Geoderma 193-194:117-121.
International Search Report and Written Opinion PCT/US2017/059076 (WO 2018/081727) (2018) (13 pages).
Jenkinson, B. (2002) "*Indicators of Reduction in Soils (IRIS): A visual method for the identification of hydric soils*," Ph.D. diss. Purdue Univ., West Lafayette, IN (p. 63-175).
Jenkinson, B. et al. (2006) "*Development and Evaluation of Iron-coated Tubes that Indicate Reduction in Soils*," Soil Sci. Soc. Am. J. 70:183-191.
McKenzie, R.M. (1971) "*The Synthesis of Birnessite, Cryptomelane, and Some Other Oxides and Hydroxides of Manganese*," Mineral. Mag. 38:493-502.
Megonigal, J. et al. (2013) "*Reduction-Oxidation Potential and Oxygen*," In: Methods in Biogeochemistry of Wetlands, DeLaune, R.D, editors, SSSA Book Ser. 10. SSSA, Madison, WI. p. 71-85.
National Research Council (1995) "*Wetlands: Characteristics and Boundaries*," Natl. Acad. Press, Washington, DC. (pp. 1-308).
National Technical Committee for Hydric Soils (2015) Technical standards for hydric soils, Tech. Note 11, NRCS, Washington, DC. (pp. 1-23).
Patrick, W.H. et al. (1996) "*Redox Measurements of Soils*," In: Methods of Soil Analysis. Part 3 (Sparks, D.L., editor) SSSA Book Ser. 5. SSSA and ASA, Madison, WI.; pp. 1255-1273.
Rabenhorst, M. C. et al. (2008) "*Iron Oxyhydroxide Reduction in Simulated Wetland Soils: Effects of Mineralogical Composition of IRIS Paints*," Soil Sci. Soc. Am. J. 72:1838-1842.
Rabenhorst, M.C. et al. (2008) "*Synthesized Iron Oxides used as a Tool for Documenting Reducing Conditions in Soils*," Soil Sci. 173:417-423.
Rabenhorst, M.C. et al. (2009) "*Measurements of Soil Redox Potential*," Soil Sci. Soc. Am. J. 73:668-674.
Rabenhorst, M.C. et al. (2017) "*A Synthesized Manganese Oxide for Easily Making Durable Manganese-Coated IRIS Tubes*" Soil Sci. Soc. Am. J. doi:10.2136/sssaj2016.10.0348n (7 pages).
Rabenhorst, M.C. et al. (2018) "*Manganese Oxides for Environmental Assessment*", Soil Sci. Soc. Am. J. dol: 10.2136/sssaJ2017.08.0256 (10 pages).
Rabenhorst. M.C. "*Manganese Oxides as an Indicator of Reduction in Soils (IRIS)*," Phoenix Convention Center North, Exhibit Hall CDE (Nov. 9, 2016) (2 pages).
Rabenhorst, M.C. (2008) "*Protocol for using and interpreting IRIS tubes*," Soil Surv. Horiz. 49:74-77.
Rabenhorst, M.C. (2009) "*Making Soil Oxidation-Reduction Potential Measurements using Multimeters*," Soil Sci. Soc. Am. J. 73:2198-2201.
Rabenhorst, M.C. (2010) "*Visual Assessment of IRIS Tubes in Field Testing for Soil Reduction*," Wetlands 30:847-852.
Rabenhorst, M.C. (2012) "*Simple and Reliable Approach for Quantifying IRIS Tube Data*," Soil Sci. Soc. Am. J. 76:307-308.
Rabenhorst, M.C. (2018) "*A System for Making and Deploying Oxide-Coated Plastic Films for Environmental Assessment of Soils*", Soil Sci. Soc. Am. J. doi: 10.2136/sssaj2018.05.0178.

(56) References Cited

OTHER PUBLICATIONS

Rabenhorst, M.C. et al. (2006) "*Synthetic Iron Oxides as an Indicator of Reduction in Soils (IRIS)*," Soil Sci. Soc. Am. J. 70:1227-1236.

Stiles, C.A. et al. (2010) "*Initial Field Installation of Manganese Indicators of Reduction in Soils*, Brooks Range, Alaska," Soil Surv. Horiz. 51:102-107.

USDA—NRCS (2010) "*Field Indicators of Hydric Soils in the United States*," Version 7.0. NRCS, Washington, DC (2 pages).

USDA—NRCS (2014) "*Hydric Soils: Introduction*," NRCS, Washington, DC (1 page).

Vorenhout, M. et al. (2004) "*Automated and Continuous Redox Potential Measurements in Soil*," J. Environ. Qual. 33:1562-1567.

Definition: "unconsolidated" (2022), Merriam-Webster.com, retrieved Mar. 25, 2022, from https:www.merriam-webster.com/dictionary/unconsolidated.

USDA, Glossary of Soil Survey Terms, Oct. 2015 (51 pages).

\* cited by examiner

Fig. 7A

Hinged plexiglass plate

Figure 11:
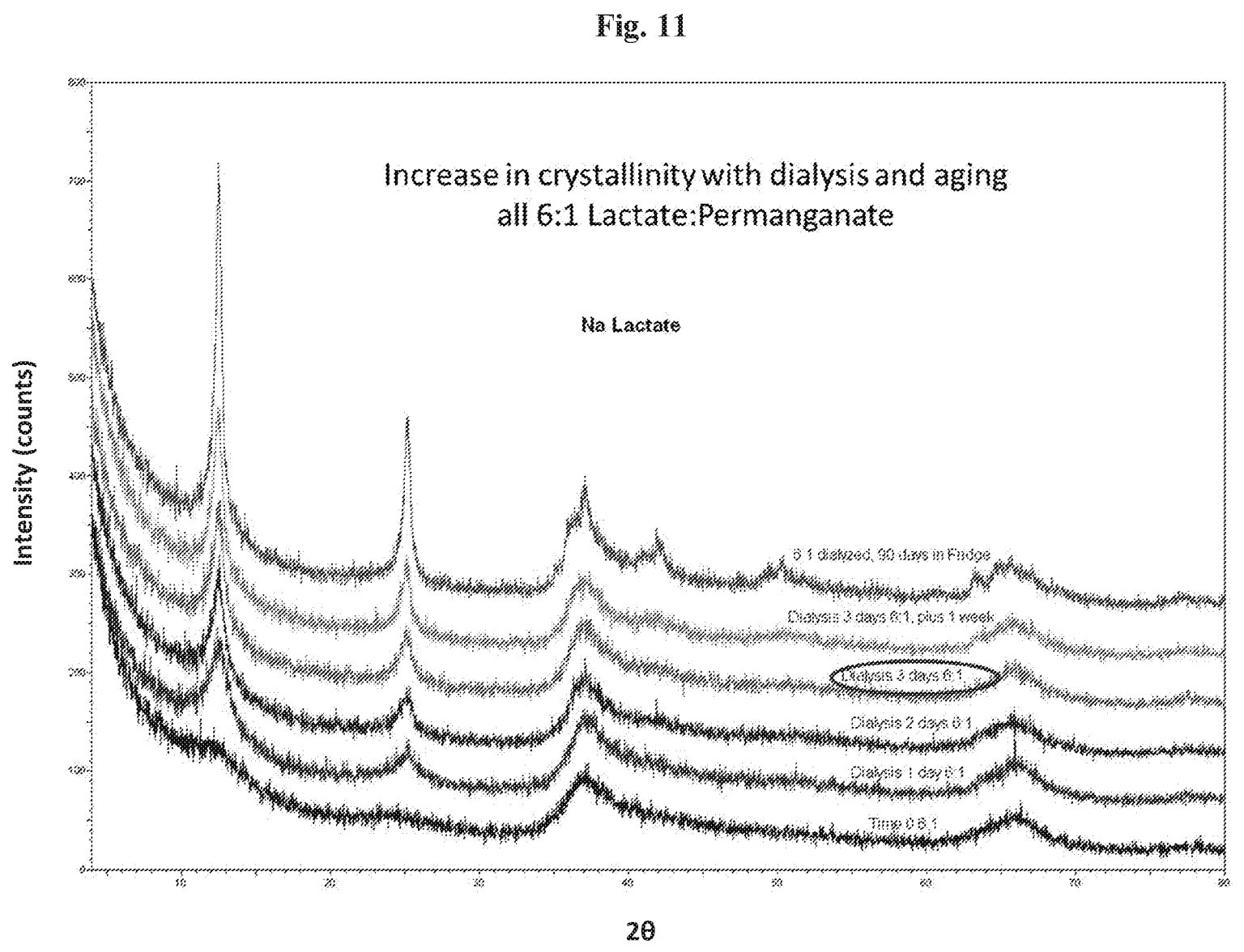

Increase in crystallinity with dialysis and aging
all 6:1 Lactate:Permanganate

Na Lactate 0 1 dialyzed, 90 days in Fridge
Dialysis 3 days 6:1, plus 1 week
Dialysis 3 days 6:1
Dialysis 2 days 6:1
Dialysis 1 day 6:1
Time 0 6:1

Intensity (counts)

2θ

SYSTEMS, METHODS AND INDICATOR MATERIALS FOR ASSESSING REDUCTION STATE IN SOILS

CROSS-REFERENCE TO RELATED APPLICATIONS

This application is a continuation application of U.S. patent application Ser. No. 16/340,274 (filed Apr. 8, 2019; pending), which application is a § 371 Application of PCT/US2017/059076 (filed Oct. 30, 2017; expired), which application claims priority to U.S. Provisional Patent Application Ser. No. 62/414,853 (filed Oct. 31, 2016), entitled "Synthetic Manganese Oxide and its use for Environmental Assessment," and U.S. Provisional Patent Application Ser. No. 62/517,628 (filed Jun. 9, 2017), entitled "System for Making/Deploying/Assessing Coated Plastic Films (CPFs) for Environmental Assessment of Soils or other Unconsolidated Materials"), each of which applications is incorporated herein by reference in its entirety.

FIELD OF THE INVENTION

The present invention relates to an indicator system for assessing a reduction state of unconsolidated material, and preparation and/or deployment of an indicator device or reactive coating comprising a manganese oxide.

BACKGROUND OF THE INVENTION

Wetlands are those ecosystems that are frequently saturated by water and populated with plants adapted to saturated soils (National Research Council (1995) "Wetlands: Characteristics and boundaries," Natl. Acad. Press, Washington, DC.). In the saturated soils, when organic materials are oxidized by heterotrophic microbes, it typically leads to anaerobic or reducing conditions that mediate a host of other biogeochemical processes. In such conditions, anaerobic microorganisms use compounds such as nitrate, manganese (Mn) oxides and/or iron (Fe) oxides as at electron acceptor instead of oxygen in respiration processes. A byproduct of this microbial activity is the increased mobility of manganese and iron in the soil solution. Saturated (hydric) soils of wetlands develop anaerobic conditions in the near surface zone (USDA-NRCS (2010) "Field indicators of hydric soils in the United States," Version 7.0. NRCS, Washington, DC; USDA-NRCS (2014) "Hydric soils: Definition," NRCS, Washington, DC). Electrochemically reducing conditions are one of the hallmark and defining features of wetland soils.

The documentation of reducing conditions in soils is therefore important in the study, monitoring, and delineation of hydric soils and wetlands. Various approaches have been developed to measure or document reducing conditions. Electrochemical potentials (voltages) can be measured (as Eh) using platinum electrodes in conjunction with a high resistance meter (Bohn, H. L (1971) "Redox potentials," Soil Sci. 112:39-45; Patrick et al. (1996) "Redox measurements of soils," In: Sparks, D. L., editor, Methods of soil analysis. Part 3. SSSA Book Ser. 5. SSSA and ASA, Madison, WI. p. 1255-1273; Vorenhout et al. (2004) "Automated and continuous redox potential measurements in soil," J. Environ. Qual. 33:1562-1567; Rabenhorst, M. (2009) "Making soil oxidation-reduction potential measurements using multimeters," Soil Sci. Soc. Am. J. 73:2198-2201; Rabenhorst et al. (2009) "Measurements of soil redox potential," Soil Sci. Soc. Am. J. 73:668-674; Megonigal, J. and Rabenhorst, M.

(2013) "Reduction-oxidation potential and oxygen," In: DeLaune, R. D., editors, Methods in biogeochemistry of wetlands. SSSA Book Ser. 10. SSSA, Madison, WI. p. 71-85). When combined with pH measurements, these data can be used to estimate the types of electrochemical transformations that will occur in the soil. Colorimetric dyes like $\alpha$-$\alpha$-dipyridyl can also be used to document the presence of reduced (ferrous) iron in the soil solution (Childs, C. W. (1981) "Field tests for ferrous iron and ferric-organic complexes (on exchange sites or in water-soluble forms) in soils," Aust. J. Soil Res. 19:175-180). However, such approaches have limitations due to either the need for specialized equipment or the difficulty in obtaining the necessary chemicals.

More recently, indicators of reduction in soil (IRIS) technology has been developed whereby an iron oxide coating is applied to PVC tubes. The iron oxide coated tubes are then inserted into the soil. Under reducing conditions, actively respiring microorganisms transfer electrons to the thin coating of iron oxide on the tube, causing the iron to become reduced and soluble, exposing portions of the underlying white color of the bare PVC tubes. The degree to which the PVC tubes become stripped of the iron oxide coating is an indication of the degree to which microorganisms were using the iron oxide as an alternate electron acceptor (Jenkinson, B. (2002) "Indicators of Reduction in Soils (IRIS): A visual method for the identification of hydric soils," Ph.D. diss. Purdue Univ., West Lafayette, IN.; Castenson, K. and Rabenhorst, M. (2006) "Indicator of Reduction in Soil (IRIS): Evaluation of a new approach for assessing reduced conditions in soil," Soil Sci. Soc. Am. J. 70:1222-1226; Jenkinson, B and Franzmeier, D. (2006) "Development and evaluation of Fe coated tubes that indicate reduction in soils," Soil Sci. Soc. Am. J. 70:183-191; Rabenhorst, M and Burch, S. (2006) "Synthetic iron oxides as an Indicator of Reduction in Soils (IRIS)," Soil Sci. Soc. Am. J. 70:1227-1236; Rabenhorst, M. (2008) "Protocol for using and interpreting IRIS tubes," Soil Surv. Horiz. 49:74-77; Rabenhorst et al. (2008) "Iron oxyhydroxide reduction in simulated wetland soils: Effects of mineralogical composition of IRIS paints," Soil Sci. Soc. Am. J. 72:1838-1842; Rabenhorst et al. (2008) "Synthesized iron oxides used as a tool for documenting reducing conditions in soils," Soil Sci. 173:417-423). When the iron oxide coating has been stripped to some prescribed degree (e.g., 30% removal within a 15-cm zone within the upper 30 cm of the ground), this is deemed by the National Technical Committee for Hydric Soils (NTCHS) as diagnostic for reducing soil conditions (National Technical Committee for Hydric Soils, 2015. Hydric Soils Tech. Note 11: Hydric Soils Technical Standard and Data Submission Requirements for Field Indicators of Hydric Soils, in USDA: (Ed.): USDA-NRCS, Washington, DC.; Rabenhorst, M. (2008) "Protocol for using and interpreting IRIS tubes," Soil Surv. Horiz. 49:74-77; Rabenhorst, M. (2010) "Visual assessment of IRIS tubes infield testing for soil reduction," Wetlands 30:847-852; Rabenhorst, M. (2012) "Simple and reliable approach for quantifying IRIS tube data," Soil Sci. Soc. Am. J. 76:307-308). IRIS devices are relatively easy to interpret and are less prone to difficulties as compared to prior methods of assessing reducing soil conditions.

IRIS technology has therefore moved from the periphery into more common use in hydric soil studies, especially after IRIS tubes were approved for use by the National Technical Committee for Hydric Soils (NTCHS). However, there are several challenges when using conventional IRIS tubes. Conventional IRIS tubes are susceptible to abrasion or scratching of the reactive coating during transport to or from the location of deployment. IRIS tubes are also prone to abrasion and scratching upon deployment into soil, especially in sandy soil conditions. Abrasion and scratching of the exterior coating adversely impacts testing capabilities, and may even render the device and data derived therefrom unusable. In addition, due to their tubular configuration, it is difficult to acquire an accurate two-dimensional image from the three-dimensional cylindrical structure of conventional IRIS devices in order to collect the data from the tubes. Moreover, conventional devices are bulky and awkward to store and transport. As such, storage and transport costs are relatively high due to the weight and size of conventional devices. Long-term storage issues also arise due to the bulky nature of the devices. Furthermore, there are environmental concerns relating to the accumulation of large quantities of non-reusable plastic tubing.

There are also limitations with iron oxide coatings utilized in conventional IRIS devices. Some soil conditions become anaerobic under less reducing conditions than those required for the reduction of the iron oxide coating on conventional devices. As such, there has been an interest in developing alternative devices similar to conventional iron oxide coated tubes, but using some other coating material that reduces more easily than iron oxides. Manganese oxides represent another commonly occurring group of minerals in soils, which reduce under less strongly reducing conditions as compared to iron oxides. Stiles et al. (2010) "*Initial field installation of manganese indicators of reduction in soils, Brooks Range, Alaska*," Soil Surv. Horiz. 51:102-107, proposed generally the use of manganese in environments where iron oxide coated tubes might be slower to demonstrate the effects of moderately reducing conditions. However, Stiles et al. failed to disclose any specifics regarding the mineralogical nature of a suitable manganese oxide coating. Nor did they propose any method for the synthesis of a manganese oxide coating.

Attempts to formulate a manganese oxide paint that can be applied much like the strongly adhering iron oxide coatings (e.g., ferrihydrite-goethite paint developed for IRIS tubes as disclosed by see Rabenhorst, M and Burch, S. (2006) "*Synthetic iron oxides as an Indicator of Reduction in Soils (IRIS)*," Soil Sci. Soc. Am. J. 70:1227-1236) have not been successful. As became readily evident through testing and observation, attempts to synthesis a manganese oxide paint suitable for use on IRIS devices failed to demonstrate the adhesive strength or durability required. Coffin, C. A. (2012) "*Indicators of Reduction in Soils (IRIS) in various conditions of saturation in South Florida marl*," M. S. thesis. Univ. of Florida, Gainesville, attempted to formulate a manganese oxide paint that involved the boiling of reagents to produce birnessite $((Na,Ca)_{0.5}(Mn^{4+},Mn^{3+})_2O_4\cdot1.5H_2O)$, similar to methods reported by McKenzie, R. M. (1971) "*The synthesis of birnessite, cryptomelane, and some other oxides and hydroxides of manganese*," Mineral Mag. 38:493-502. Coffin's approach involved the use of caustic chemicals at elevated temperatures, was time consuming (requiring two or more months for preparation), and ultimately failed to produce a manganese coating that exhibited reliable and sufficient adherence and durability properties.

Synthesizing birnessite at room temperature was reported by Händel et al. (2013), which reflected an advance over previous methods requiring boiling of reagents and titrations with strong acids (see Coffin, C. A. (2012) "*Indicators of Reduction in Soils (IRIS) in various conditions of saturation in South Florida marl*," M. S. thesis. Univ. of Florida, Gainesville; McKenzie, R. M. (1971) "*The synthesis of birnessite, cryptomelane, and some other oxides and hydroxides of manganese*," Mineral Mag. 38:493-502). Following the procedure of Händel et al. (2013), Dorau, K. and Mansfeldt, T. (2015) "*Manganese-oxide-coated redox bars as an indicator of reducing conditions in soils*," J. Environ. Qual. 44:696-703, suggested the synthesis of birnessite at room temperature and use thereof in the production of manganese oxide coated IRIS tubes. However, the procedure of Dorau and Mansfeldt was difficult, extremely time consuming, and much different from the streamlined methods used for preparing iron oxide coated tubes. Moreover, Dorau and Mansfeldt observed that when the birnessite formulation was painted onto PVC tubes in the same way that iron oxide paint is applied to IRIS tubes (Rabenhorst, M and Burch, S. (2006) "*Synthetic iron oxides as an Indicator of Reduction in Soils (IRIS)*," Soil Sci. Soc. Am. J. 70:1227-1236), the manganese oxide coating failed to properly adhere and easily rubbed off. Therefore, using the birnessite formulation of Händel et al. (2013), Dorau and Mansfeldt provided for the application of multiple coatings of a relatively viscous birnessite polish (e.g., similar to the consistency of shoe polish) followed by a burnishing stroke, with application cycles repeated many times until the polished surface was dried. Thus, Dorau and Mansfeldt reported that repeated coatings and burnishing strokes were required in order to achieve a device having sufficient durability and coloration. The time required to manufacture a manganese oxide coated device in accordance with the procedures of Dorau and Mansfeldt is more than an order of magnitude greater than the time required to make an iron oxide coated tube of comparable size using conventional painting methods (Rabenhorst, M and Burch, S. (2006) "*Synthetic iron oxides as an Indicator of Reduction in Soils (IRIS)*," Soil Sci. Soc. Am. J. 70:1227-1236).

Thus, the development and use of manganese formulations for IRIS devices have been extremely problematic due to the failure of the manganese coating to properly adhere to the IRIS substrate and remain durable against rubbing and abrasion and/or due to the time-consuming and cumbersome techniques proposed. Therefore, there is a need to develop systems, methods and indicator materials for IRIS devices that overcome some or all of the difficulties and limitations of conventional approaches.

SUMMARY OF THE INVENTION

The present invention relates to a systems and methods for preparing and/or deploying IRIS devices. In some embodiments, the systems and methods provide for coding, tracking, mapping of deployment locations, image acquisition, quantification, analysis and interpretation of devices and data obtained therefrom. The present invention also relates to an easily synthesized crystalline birnessite coating or paint, that can be used to quickly make IRIS devices with a strongly adhering and durable manganese-oxide coating. In preferred embodiments, a large excess of sodium lactate is utilized to reduce $KMnO_4$ quickly, followed by centrifuge washing and dialysis, e.g., 3 days (see, e.g., FIGS. 8-16). Consistency of the reduced solution may be adjusted by adding water. The resulting birnessite composition may be applied (e.g., such as by painting using a brush and lathe-type device) to an IRIS device. Approximately 30 IRIS devices (e.g., PVC tubes) can be prepared in as little as 1 hour. The manganese oxide coating tubes become solubilized and stripped from PVC tubes more rapidly, and under less strongly reducing conditions, as compared to Fe oxide coatings (see, e.g., FIG. 6).

The present invention is directed to an indicator system for assessing a reduction state of unconsolidated material. The system comprises a delivery tube having opposing first and second ends, an exterior wall extending between the first and second ends, and an interior chamber defined by the exterior wall and accessible through the opposing ends. A substrate is provided which is disposed within the interior chamber, and includes a first major surface having a reactive coating thereon. The reactive coating is at least partially removable from the first major surface upon exposure to a reducing condition of unconsolidated material over a period of time (see, e.g., FIG. 3).

In some embodiments, the substrate comprises a flexible polymer film. In some implementations, the film has a thickness from about 2 mil to about 30 mil, or from about 2 mil to about 30 mil, or from about 5 mil to about 20 mil, or from about 10 mil to about 20 mil. The system may include a loading tube receivable in the interior chamber. The film is disposable around the loading tube for insertion with the loading tube into the interior chamber.

In some embodiments, the reactive coating comprises an iron oxide or a manganese oxide. In some implementations, the reactive coating comprises a dried residue of a manganese oxide reduced from a solution of Na lactate and potassium permanganate ($KMnO_4$) having Na lactate:$KMnO_4$ molar ratio of greater than about 2.0. In some implementations, the Na lactate:KMnO4 molar ratio is greater than about 6.0 (see, e.g., FIGS. 9 and 10). In some implementations, the Na lactate:KMnO4 molar ratio is between about 2.0 and about 22.0, or between about 2.0 and about 11.0, or between about 2.0 and about 8, or between about 4.0 and about 8.0, or between about 6.0 and about 8.0, e.g., such as 6.7.

In some embodiments, the delivery tube comprises a transparent or translucent material, so that the substrate and/or loading tube is readily visible through the delivery tube. In some implementations, the substrate comprises a machine-readable identifier code associated with information relating to the substrate, including but not limited to deployment location, deployment and/or retrieval date, deployment and/or retrieval time, the reactive coating, and/or determined reduction state or other information gathered from the device.

In some embodiments, the system includes a substrate holder including a planar surface configured for receiving and retaining the substrate in a substantially planar orientation. The holder preferably includes a transparent cover plate disposable over the substrate when retained on the planar surface. The holder is configured to retain and position a collected substrate, e.g. such as for image acquisition and assessment (see, e.g., FIG. 7A).

In some embodiments, the substrate comprises a polymer material selected from group consisting of polyethylene terephthalate (PET or PETE), high-density polyethylene (HOPE), polyvinyl chloride (PVC), low-density polyethylene (LOPE), polypropylene (PP), polystyrene (PS), vinyl, mylar, acetate, polyvinylidene fluoride, and polycarbonate.

In some embodiments, the system includes a push or retaining rod including an engagement portion configured to releasably couple to an engagement portion disposed on the substrate (e.g., such a hook member and hole in the substrate). The delivery tube is removable from the substrate and the substrate is retainable in a fixed position via the retaining rod (see, e.g., FIG. 4).

The present invention is also directed to a method of preparing an indicator device for assessing a reduction state of unconsolidated material, comprising the steps of: providing a substrate including a major surface having a reactive coating thereon, said reactive coating at least partially removable from said first major surface upon exposure to a reducing condition of unconsolidated material over a period of time; inserting said substrate into an interior chamber of a delivery tube to form a deployable indicator device, said delivery tube having opposing first and second ends, and an exterior wall extending between said first and second ends and defining said interior chamber, and wherein said substrate is removable from said interior chamber through openings in said first and second ends (see, e.g., FIG. 3).

In some embodiments, the method provides for a substrate comprising a flexible polymer film, and includes the additional steps of: wrapping said film around a loading tube prior to said inserting step; and extracting said loading tube from said delivery tube to form said deployable indicator device. The disclosed methods may also provide for: inserting said indicator device into unconsolidated material; and extracting said delivery tube from the unconsolidated material while maintaining said substrate in the unconsolidated material.

The present invention is also directed to a method of producing a manganese oxide coating, comprising: reducing a potassium permanganate ($KMnO_4$) solution using sodium (Na) lactate, wherein Na lactate:$KMnO_4$ molar ratio is greater than about 2.0. In some implementations, the Na lactate:KMnO4 molar ratio is greater than about 6.0 (see, e.g., FIGS. 9 and 10). In some implementations, the Na lactate:$KMnO_4$ molar ratio is between about 2.0 and about 22.0, or between about 2.0 and about 11.0, or between about 2.0 and about 8, or between about 4.0 and about 8.0, or between about 6.0 and about 8.0, e.g., such as 6.7.

In some embodiments, the method provides for the additional step of removing excess Na lactate after reducing via one or more washing cycles and/or dialyzing the KMnO4 solution after reducing and/or centrifuge washing. In some implementations, the reaction time is less than about 120 minutes, e.g., between 10 and 120 minutes (see, e.g., FIGS. 11, 12 and 15).

BRIEF DESCRIPTION OF THE DRAWINGS

FIG. 7A illustrates as an exemplary holder configured to secure and flatten a plastic film, and FIG. 7B illustrates an exemplary image capture jig configured to position and align and film relative to an image capture device.

FIG. 8 illustrates total mass of birnessite synthesized from 10 g of $KMnO_4$ by adding sodium (Na) lactate at molar ratios of 0.89, 1.12, 1.34, and 2.23. No significant difference among the four treatments was observed, and the mean recovery was 99.5% of the predicted amount (6.84 g). Also shown is the volume of the sediment cake from a 25 mL sample of suspension (containing a total of 0.454 g birnessite) that was centrifuged for 15 min at 10,000 G. Samples from one set were centrifuged 4 days after synthesis and immediately out of dialysis, and those from the other set were centrifuged 39 days after synthesis and 35 days out of dialysis.

FIG. 11 shows via X-ray diffraction patterns a change in crystallinity of the birnessite synthesized (2 hour reaction followed by 3 days of dialysis) by reducing 0.063 M $KMnO_4$ with Na lactate to $KMnO_4$ ratio of 6.7 during the period from initial synthesis, the 3 days of dialysis, and subsequent sample storage.

DETAILED DESCRIPTION OF EMBODIMENTS OF THE INVENTION

Figure 1:
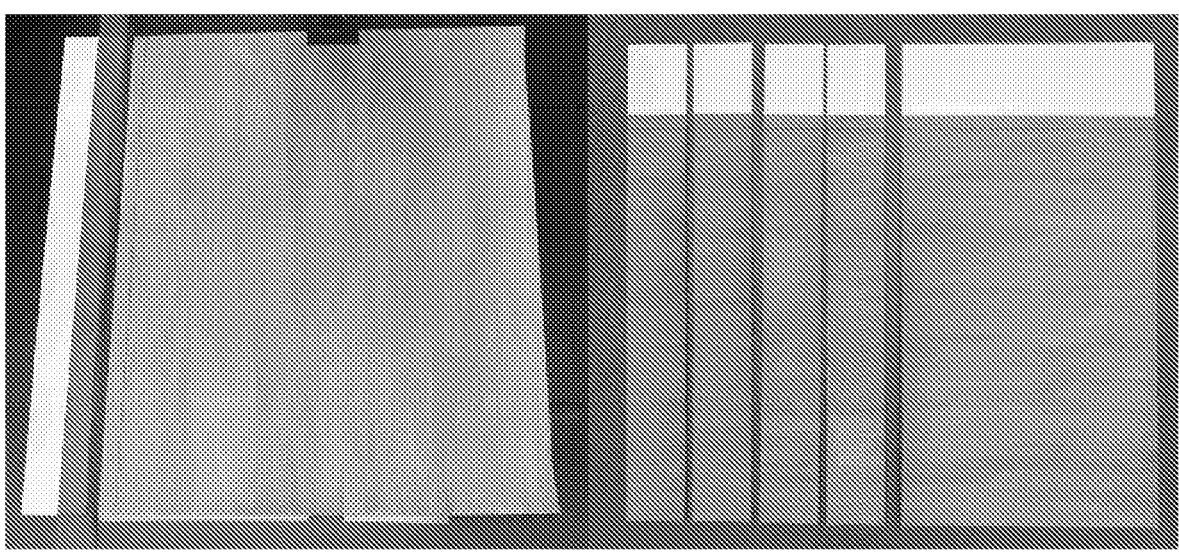
FIG. 1 is an image of a large sheet of flexible plastic film (left panel) coated with a reactive oxide paint (e.g., iron oxide paint or manganese oxide paint), and showing the sheet of flexible film cut into strips (right panel) suitably sized for use with an IRIS system in accordance with the present invention.

The present invention is directed to systems and methods for deploying an IRIS film that overcomes many of the challenges associated with conventional IRIS devices. In some embodiments, the systems and methods provide for coding, tracking, mapping of deployment locations, image acquisition, quantification, analysis and interpretation of IRIS devices and data obtained therefrom. In accordance with disclosed embodiments, a system is provided for installing thin plastic films in unconsolidated materials (e.g., soil, compost, mine tailings, sediment, manure, etc.) for the purpose of conducting environmental assessment. The plastic films may be coated with any sensitive or reactive material, e.g. such as a composition comprising iron oxide or a mixture of iron oxides (ferrihydrite-goethite as described in U.S. Pat. No. 7,550,297, the disclosure of which is incorporated herein by reference) or with a manganese oxide or mixture of manganese oxides, such as disclosed herein. The plastic film is inserted into unconsolidated material for the purpose of assessing environmental conditions thereof. For example, the disclosed systems provide for the assessment and documentation of soil reduction (low redox potential) or chemical reactions between the coatings and other chemical compounds in the soil such as soluble sulfides.

The disclosed systems and methods provide for the installation of flexible coated plastic films into the soil from above with a minimal disturbance to the medium into which they are inserted, that protects the coating against abrasion during installation, and ensures an intimate contact between the coated plastic film and the surrounding medium. The system therefore overcomes many of the limitations of conventional IRIS devices, such as the device disclosed in U.S. Pat. No. 6,766,762, which are prone to abrasion and scratching, and are bulky and difficult to transport and store.

In some embodiments, the system provides for coding, tracking, mapping, storing, archiving, analyzing and/or interpreting data obtained from the IRIS devices of the present invention. In preferred embodiments, the IRIS device is a flexible coated polymer film. The systems and methods of the present invention provide numerous advantages over prior methodologies. Once the coated plastic films have been prepared for deployment (loaded into the delivery tubes), they are protected against scratching or abrasion during storage and transport. In addition, during insertion of the coated plastic films into a medium, the delivery tubes provide protection against abrasion by the medium (such as sandy soil) during the actual deployment. Therefore, scratching of the coated films is substantially reduced as compared to conventional techniques.

Moreover, the weight of a coated plastic film is only about an eighth (~12.3%) of that of a half-inch schedule 40 PVC tube (used for most conventional IRIS devices), and about an eighteenth (~5.5%) of the weight of a PVC rod with the same outer diameter (OD) of 0.84 inch. As such, it is much easier to transport the devices of the present invention, and the cost of transport substantially reduced, as compared to conventional PVC tubes or rods. Moreover, the volume required to store the coated plastic films of the present invention is only about one twenty-third (~4.3%) of that required to store conventional PVC tubes or rods. Therefore, the space required to store the coated plastic films of the present invention is a fraction of that required to store conventional PVC tube/rod devices.

Two-dimensional images are easily obtained from coated plastic films, which are much more difficult to obtain as compared to conventional cylindrical rods or tubes. Therefore, digital images of the paint removal patterns are easy to acquire and to store. Furthermore, in contrast to conventional coated PVC tubes that are usable only once, the delivery tubes utilized in the deployment of the coated plastic films of the present invention are completely reusable.

The present invention is also directed to a method of synthesizing manganese oxide composition in a water suspension, which can be quickly and easily applied to an IRIS device, such as for example a polymer tube or film. The resulting manganese oxide coating exhibits excellent adhesive properties and durability against rubbing and abrasion after drying. The manganese oxide coated devices are suitable for environmental applications such as assessment of reducing conditions in soils, and in the sorption of various chemicals of concern such as heavy metals (Dorau et al. (2015) "*Comparison of manganese and iron oxide-coated redox bars for characterization of the redox status in wetland soils*," Wetlands 36:133-141).

Formulations of iron oxides are suitable for use as reactive coatings on IRIS tubes. Iron oxide suspensions may be applied or painted onto a PVC tube as the tube is rotated (e.g., utilizing a lathe device). The iron oxide suspensions are readily applied on the tubes, e.g., using a foam brush, sprayer, or other application device, thereby quickly and easily coating the tube. For example, coating a PVC tube having a length of 50 cm using rotation and painting method may be accomplished in less than about 2 minutes. Although techniques for applying an manganese oxide coating have been proposed (see Dorau, K. and Mansfeldt, T. (2015) "*Manganese-oxide-coated redox bars as an indicator of reducing conditions in soils*," J. Environ. Qual. 44:696-703), such techniques are much more complicated and time consuming as compared to conventional methods utilized for the application of iron oxide suspensions. As noted above, Dorau and Mansfeldt demonstrated that manganese oxide coated tubes could be prepared from very poorly crystalline birnessite (synthesized using the formulation of Händel et al. (2013) "*A simple method to synthesize birnessite at ambient pressure and temperature*," Geoderma 193-194:117-121, but the manganese coating was only durable if the manganese formulation was applied as a thick polish, followed by a burnishing stroke, and repeated many times until the polished surface became dried during the process. However, when the conventional birnessite formulation (Dorau, K. and Mansfeldt, T. (2015) "*Manganese-oxide-coated redox bars as an indicator of reducing conditions in soils*," J. Environ. Qual. 44:696-703; Händel et al. (2013) "*A simple method to synthesize birnessite at ambient pressure and temperature*," Geoderma 193-194:117-121) is applied to a using a bush and lathe device (e.g., as typically done when producing iron-coated IRIS tubes), the manganese-coating exhibits poor durability (scale of 1 out of 5) and easily rubs off.

In accordance with disclosed embodiments, a manganese oxide formulation is provided that exhibits substantially better durability and adhesive qualities as compared to prior manganese formulations. The present invention provides for a method synthesizing an increased crystalline birnessite manganese oxide ($(Na,K)_{0.5}(Mn^{4+},Mn^{3+})_2O_4 \cdot 1.5H_2O$), that may be easily and rapidly applied to an IRIS device (e.g., such as PVC tubing with a brush and lathe device arrangement). The manganese oxide coating has excellent durability (5 on a scale of 1-5).

Increased crystallinity, as compared to prior manganese oxide formulations, was shown by X-ray diffraction. In contrast, methods disclosed by Händel et al. (2013) "*A simple method to synthesize birnessite at ambient pressure and temperature*," Geoderma 193-194:117-121, and Dorau, K. and Mansfeldt, T. (2015) "*Manganese-oxide-coated redox bars as an indicator of reducing conditions in soils*," J. Environ. Qual. 44:696-703, formed very poorly crystalline birnessite by reducing $Mn^{7+}$ in 0.063 M $KMnO_4$ solution using 50% Na lactate in proportions such that the molar ratio of Na lactate to potassium permanganate was approximately 0.9. In accordance with procedures disclosed by Händel et al. (2013) "*A simple method to synthesize birnessite at ambient pressure and temperature*," Geoderma 193-194: 117-121, 1 ml 50% Na lactate was added to 100 ml of a 0.063 M $KMnO_4$ solution (which was itself prepared by adding 1 g $KMnO_4$ to 100 ml water). The solution/suspension was stirred and allowed 2 hours reaction time. The solid manganese oxide was centrifuge washed 5 times to remove any remaining solutes.

In contrast, disclosed methods provide for the synthesize of a much more crystalline birnessite by dramatically increasing the ratio of lactate to permanganate, and the ratio of Na to K to greater than 2.2 (typically 6.7). This was accomplished by adding 6 ml 60% Na lactate to 100 ml of a 0.063 M $KMnO_4$ solution (which is itself prepared by adding 1 g $KMnO_4$ to 100 ml water). The solution/suspension was stirred for 2 hours, after which the solid phase manganese oxide was centrifuge washed 3 times with de-ionized (DI) water and then dispersed and transferred to dialysis tubing which was placed into a basin of DI water where it is dialyzed for 3 days (DI water replaced every 12 hours).

The birnessite that is synthesized in accordance with disclosed methods is substantially more crystalline as compared to prior formulations, as evidenced by: 1) much sharper XRD peaks (002, 212, 161, 544/611 reflections); and 2) the observation of a number of additional XRD peaks (153, 253/324, 443/316, and 446 reflections) not visible when the birnessite is synthesized according to prior procedures such as disclosed by Händel et al. (2013) "*A simple method to synthesize birnessite at ambient pressure and temperature*," Geoderma 193-194:117-121.

When the suspension is removed from dialysis, it is centrifuged at approximately 1000 G for 5 minutes and decanted. The resulting cake in the bottom of the tube is then loosed and homogenized using a using a vortex mixer and/or stirring so that the consistency of the manganese oxide suspension is similar to that of heavy cream or thin yogurt. A small amount of water may be added to achieve the desired consistency. A coating of the resulting birnessite was applied to rotating PVC tubing (0.5 inch schedule 40 PVC tubing 9, including an outer diameter of 2.1 cm and length of 50 cm) using a foam brush and lathe-type device rotating at about 100 rpm. The coating process was completed in about 1 minute.

The manganese oxide coating was allowed to dry overnight, and subsequently evaluated. Durability of the manganese oxide coating was excellent (5 on a scale of 1-5), and substantially different as compared to prior formulations (e.g., such as formulations disclosed by Händel et al. (2013) "*A simple method to synthesize birnessite at ambient pressure and temperature*," Geoderma 193-194:117-121, which exhibits poor durability of 1 on a scale of 1-5).

Preparation of Coated Film

The thin plastic films may vary in thickness, e.g., from 0.002 inches to 0.030 inches in thickness (2 mil to 30 mil), which ensures that they are flexible. The plastic composition may comprise one or more plastic materials, including but not limited to: polyethylene terephthalate (PET or PETE), high-density polyethylene (HOPE), polyvinyl chloride (PVC), low-density polyethylene (LOPE), polypropylene (PP) polystyrene (PS), vinyl, mylar, acetate, polyvinylidene fluoride, and polycarbonate. In preferred embodiments, the plastic films comprise polypropylene or vinyl (PVC), which exhibit superior adhesiveness of iron oxide and manganese oxide coatings relative to other plastics.

The films may be prepared by coating (e.g., painting) small pieces of plastic film already the approximate size for installation (e.g., 3 inch by 24 inch) or by coating larger sheets (e.g., 24 inch by 24 inch, or larger). After the coated films have dried, they may be cut to a desired size for installation (FIG. 1). The film to be coated is attached (e.g, such as by adhesive strips) to a smooth surface and the prepared for painting or coating using, for example, a brush (a bristle brush, or more preferably a foam brush), a roller, a sprayer or other applicator.

Figure 2:
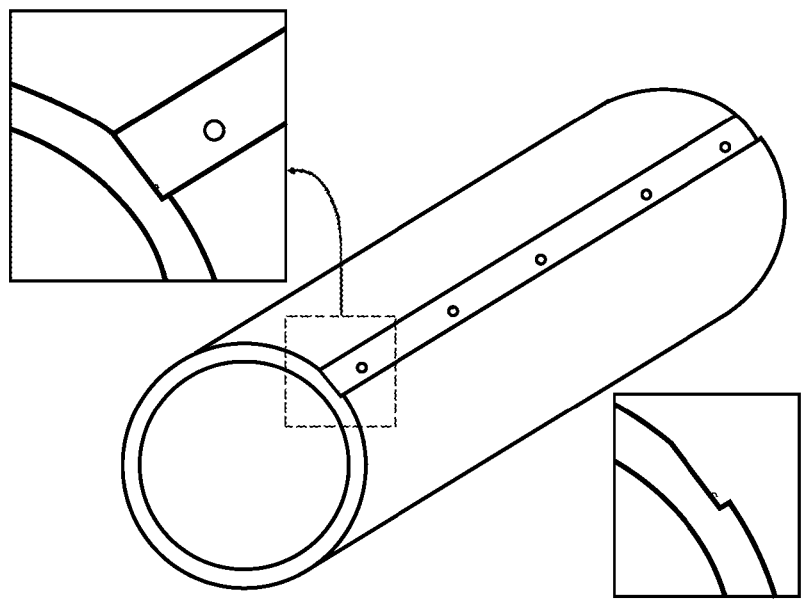
FIG. 2 illustrates an exemplary film wrapped around a cylinder or drum to facilitate the coating process of the film, wherein the film may be painted using a brush, roller, sprayer or other application device as the drum is rotated. An exploded perspective view of a boxed portion of the filmed wrapped drum (shown in dashed line) is shown in the upper inset, and a cross-sectional view of boxed portion is shown in the lower inset.

Application, particularly on cylindrical support or drum, may be facilitated though the use of a lathe-like device that is utilized to slowly rotate the surface and thereby facilitate an even coating. After application, the coatings are preferably permitted to dry or cure (e.g. in air and it room temperature, or via applied heat, such as with a heated blow dryer). The film may be secured to the cylindrical drum using, for example, adhesive strips or other securing mechanisms. The drum and attached film may then be rotated at an appropriate speed (e.g., approximately 5 to 30 rotations per minute) using the lathe-type device. In some implementations, the film is perforated along an edge, and hooked or secured to pegs or other coupling mechanisms on the drum (FIG. 2), thereby securing the film on the drum and preventing any slippage of the film relative to the drum during rotation. The paint or coating may then be readily applied using a brush, roller, sprayer, etc., to the rotating film.

After the plastic film has been painted, it is removed and dried for a period of time (e.g., 2 to 24 hours). If the plastic film is a relatively large in size, it may be cut to a desired size (e.g., 3 inch by 24 inch) after drying.

Preparation of IRIS Film

Figure 3:
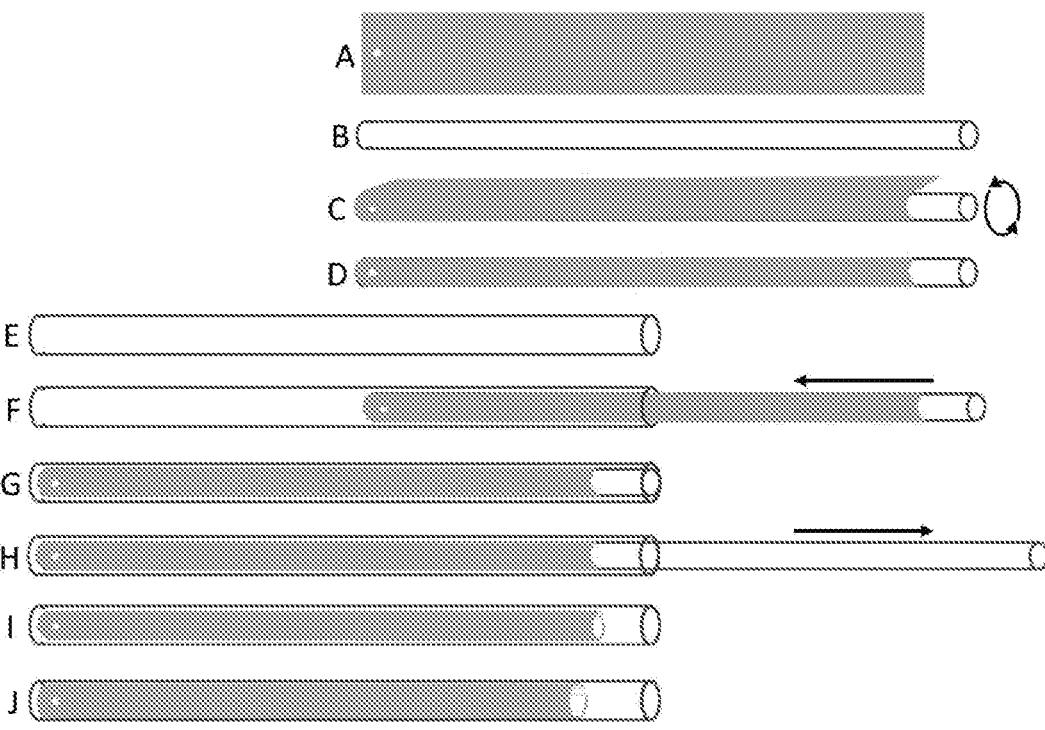
FIG. 3 illustrates schematically the preparation and loading of a flexible coated film into a delivery tube via use of a loading tube in accordance with an embodiment of the present invention. A flexible strip of coated film (panel A) is wrapped around a loading tube (panel B) with the coated reactive surface of the film facing outwardly and away from the loading tube (panel C). The film-wrapped loading tube (panel D) is then inserted into a delivery tube (panels E, F and G). The loading tube is then extracted from the delivery tube (panel H), leaving the flexible coated film inside the deliver tube (panel I). The coated film is permitted to expand against the interior surface of the delivery tube (panel J) and is retained therein until deployment of the coated film.

With the coated surface facing the outside, the film is placed into a delivery tube (e.g., 1 inch outer diameter and 7/8 inch inner diameter). The film is first wrapped around a loading tube, which has an outer diameter (e.g., 3/4 inch) that is less than the inner diameter of the delivery tube. The wrapped loading tube may then be inserted into the delivery tube. With reference to FIG. 3, panels A-J, the coated strip of coated film (panel A) is wrapped around the smaller diameter loading tube (panel B) with the coated surface facing outwardly relative to the loading tube (panel C). The film-wrapped loading tube (panel D) is then inserted into the delivery tube (panel E), which has an inside diameter larger than the film-wrapped loading tube (panels F and G). The loading tube is then extracted from the delivery tube (panel H), leaving the rolled and coated film inside the deliver tube (panel I). The coated film expands to the inner diameter of the delivery tube (panel J), and is retained therein until deployment of the coated film.

The delivery tube may be comprised of any number of plastic materials, including but not limited to: polycarbonate, polystyrene, acrylic, PVC, or another similar material. Alternatively, the delivery tube may be comprised of a metal, including but not limited to: aluminum or copper. However, in preferred embodiments, the delivery tube is comprised of a transparent or translucent material (e.g., clear polycarbonate) so that the coated film is visible when disposed therein.

Deployment of Coated Film

Figure 4:
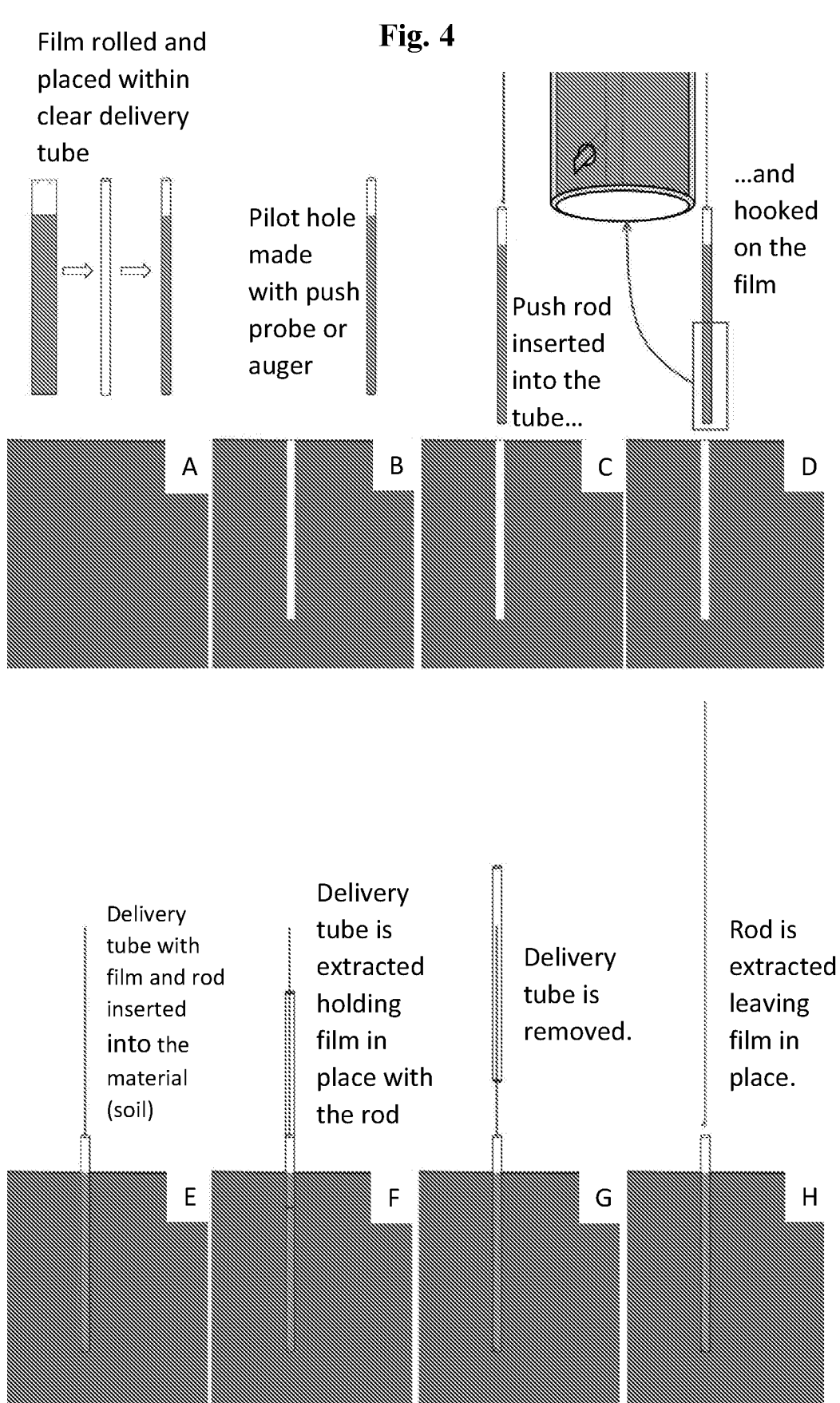
FIG. 4 illustrates schematically field deployment of a flexible coated film in accordance with a disclosed embodiment. A rolled and coated film disposed within a delivery tube (e.g., such as shown in FIG. 3, panel J) is provided for deployment into testing material (FIG. 4, panel A). A pilot hole is formed in the material to be tested (FIG. 4, panel B), wherein the pilot hole has a diameter and depth suitable for accommodating the delivery tube therein. A push rod (FIG. 4, panel C) having a length greater than the length of the delivery tube is provided. The push rod is inserted into the interior chamber of the delivery tube and engages the film (FIG. 4, panel D). The coupled delivery tube (containing the rolled film) and push rod are inserted together down in to the pilot hole (FIG. 4, panel E). Using the push rod to maintain the coated film in position within the pilot hole (e.g., such as via coupling or engagement portions as shown in the inset in panel D), the delivery tube is pulled up and out of the pilot hole so that the film is retained within the pilot hole (FIG. 4, panel F). The empty delivery tube is pulled vertically upward and out of the pilot hole (FIG. 4, panel G), and may be slid off of the push rod. The push rod is then unhooked or otherwise disengaged from the coated film, thereby leaving the coated film in place within the medium (FIG. 4, panel H).

The rolled and coated film disposed within the delivery tube is ready for deployment (FIG. 4, panel A). Prior to deployment, a pilot hole is formed in soil or other unconsolidated material to be tested (e.g., compost, mine tailings, sediment, manure, etc.). The pilot hole has a diameter and depth suitable for accommodating the outer diameter of the delivery tube (panel B). Preferably, the pilot hole has a depth greater than the length of the film to be installed (e.g., such as a depth 2-4 inches greater than the length of the film). In one implementation, the pilot hole has a depth of about 50 cm. A push rod is provided (panel C), which has a length greater than the length of the delivery tube, and preferably about twice the length of the delivery tube. The push rod includes an extruding snag or hook on a distal end thereof. The push rod is inserted into the interior chamber of the delivery tube with the extruding snag disposed inside the chamber of the delivery tube containing the file (panel C), and hooked onto a corresponding opening or otherwise connected to film (panel D).

The push rod disposed within the delivery tube so that the extruding snag is engaging the hole in the film so that the push rod and delivery tube are coupled and may be held firmly together, thereby preventing or minimizing any movement or sliding of one relative to the other. The coupled push rod and delivery tube may then be inserted together down in to the pilot hole (panel E). The coupled push rod and delivery tube are inserted into the pilot hole so that the coated plastic film within the delivery tube is inserted into the soil or material surface at a depth appropriate for testing.

Using the push rod to keep the plastic film from moving, the delivery tube is then pulled up and out of the pilot hole, so that the film is retained within the pilot hole (panel F).

Thus, the empty delivery tube is extracted from the pilot hole, and the film is retained within the pilot hole and at the appropriate depth within the medium. The empty delivery tube is pulled vertically upward and out of the pilot hole until it is entirely above the ground surface and above the film (panel G). The push rod may then be extracted from the pilot hole by disengaging or unhooking the extruding snag from the hole in the film, thereby leaving the coated plastic film in place within the medium (panel H).

Figure 5:
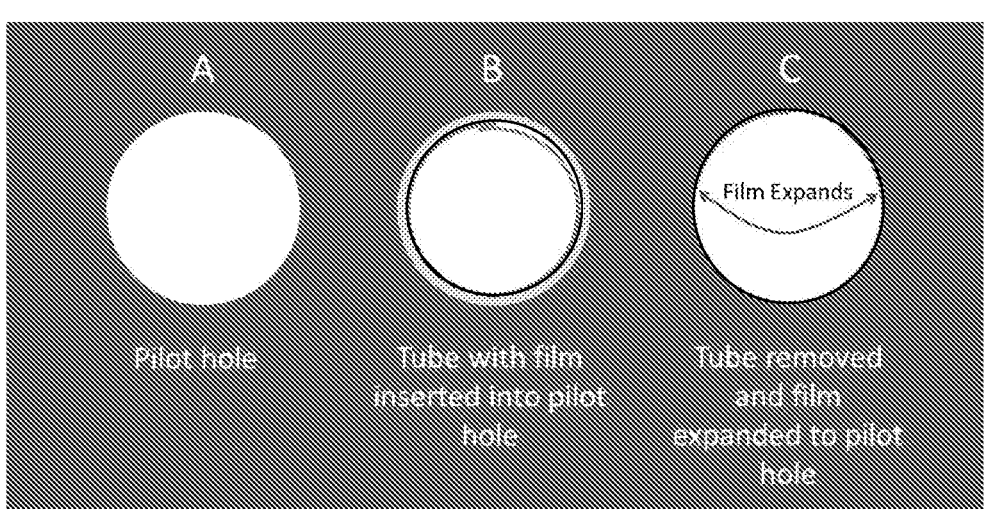
FIG. 5 illustrates schematically in cross-sectional plan view the pilot hole (panel A), delivery tube with film inserted into the pilot hole (panel B), and film expanded within and against the sides of the pilot hole after removal of the delivery tube (panel C).

A vertical or plan view of the pilot hole, delivery tube and film expanded within the pilot tube is shown in FIG. 5. A cross section of the empty pilot hole (FIG. 5, panel A) preferably has a diameter substantially equal to, or slightly larger than, the outer diameter of the delivery tube. For example, the diameter of the pilot hole and/or the delivery tube may be about 1 inch. The inserted delivery tube containing the coated plastic film may be readily inserted into the pilot hole (FIG. 5, panel B). Upon removal of the empty delivery tube (e.g., using the push rod), the film is allowed to expand or unroll against the inner surfaces of the pilot hole (FIG. 5, panel C). Thus, the film has a diameter substantially equal to the diameter of the pilot hole, thereby providing contact between the plastic film and the surrounding medium (e.g., soil).

Performance of Oxide-Coated Plastic Film

Five replicate iron oxide-coated films and five replicate manganese oxide-coated plastic films in accordance with disclosed embodiments were deployed in a seasonally saturated wetland in Caroline Co., Maryland for a 1-month period from early March 2017 to early April 2017. At the same location and at the same time, five replicate iron oxide-coated PVC tubes and five replicate manganese-oxide coated PVC tubes were also deployed into the soil. After the one-month period, all devices were retrieved and rinsed.

Figure 6:
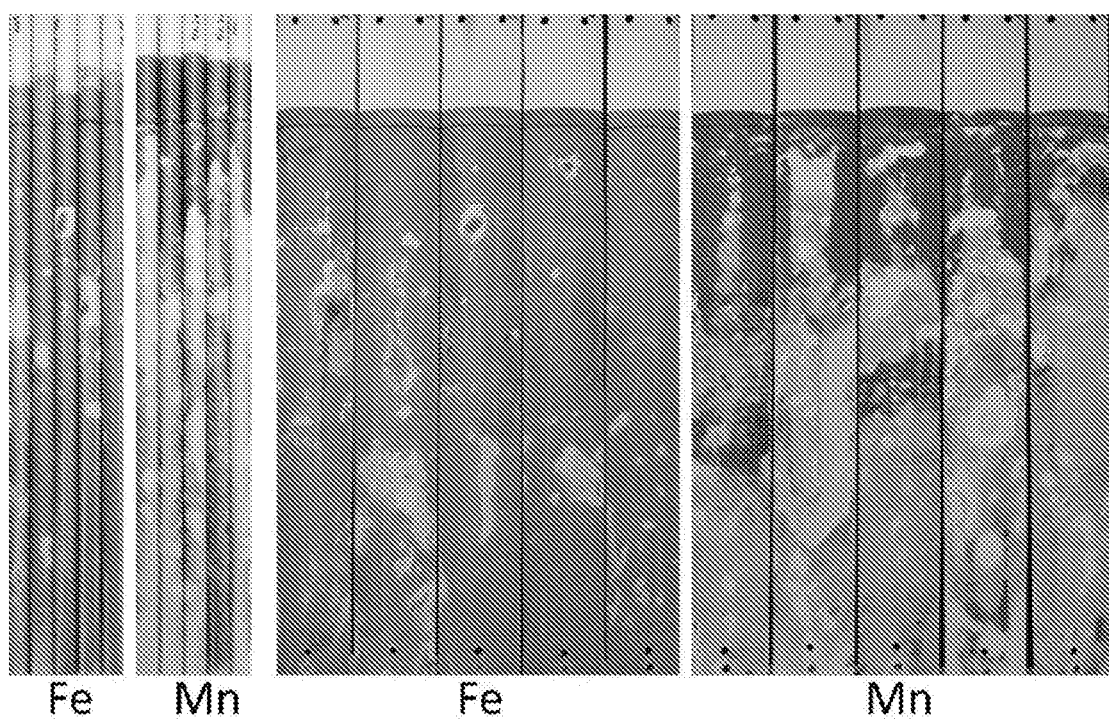
FIG. 6 are images, from left to right, of Fe oxide-coated PVC tubes, Mn oxide-coated PVC tubes, Fe oxide-coated flexible films (unrolled), and Mn oxide-coated flexible films (unrolled) after 1-month deployment in a seasonally saturated wetland area in Caroline County, Maryland.

Images of the devices after retrieval are shown in FIG. 6. Distinct differences were observed between the devices coated with manganese oxide paint versus devices coated with iron oxide paint. However, for the same type of coating, the quantities and patterns of oxide paint removal were very similar regardless of whether the coatings were deployed on PVC tubes or on plastic films.

Coding, Tracking and Mapping of Coated Film

A bar code or other identifier may be affixed to, and unique to, each film strip. Thus, the particular coating disposed on the film strip may be associated with the unique identifier. Using a computer, smartphone application, or other system in communication with the identifier, the time of deployment of the film and other information relating thereto may be readily recorded. For example, the following information may be documented: 1) the identification number from the barcode scan is recorded; 2) coordinates or deployment field site location are determined (e.g., via GPS information from a smart phone) and recorded; 3) the date and time of deployment and/or the date and time of retrieval is recorded; 4) observations or other information about the field site, project, or other pertinent information is documented; and 5) images of the field site, film or other information are documented or linked to the record (e.g., such as using a digital camera or smartphone camera).

Any pertinent information such as that noted above is provided in a single record or database entry, and may be readily stored on the device, downloaded to a storage database, and/or uploaded to a cloud-based storage site. The information is readily retrievable (e.g., using the smartphone application) by search. Alternatively, or in addition, the barcode or other identifier on the film may be scanned, which links to and retrieves the previous record relating to such identifier. Thus, site location may be accessed and/or confirmed (e.g., via GPS information), the log date and time reviewed and/or confirmed, and/or other information may be reviewed and/or confirmed relating to deployment or retrieval of a particular film. The collected data records are stored and archived, and readily searchable and accessible thereafter (e.g., such as if needed for further study, regulatory compliance, etc.).

Image Acquisition, Quantification and Analysis

Figures 7A, 7B:
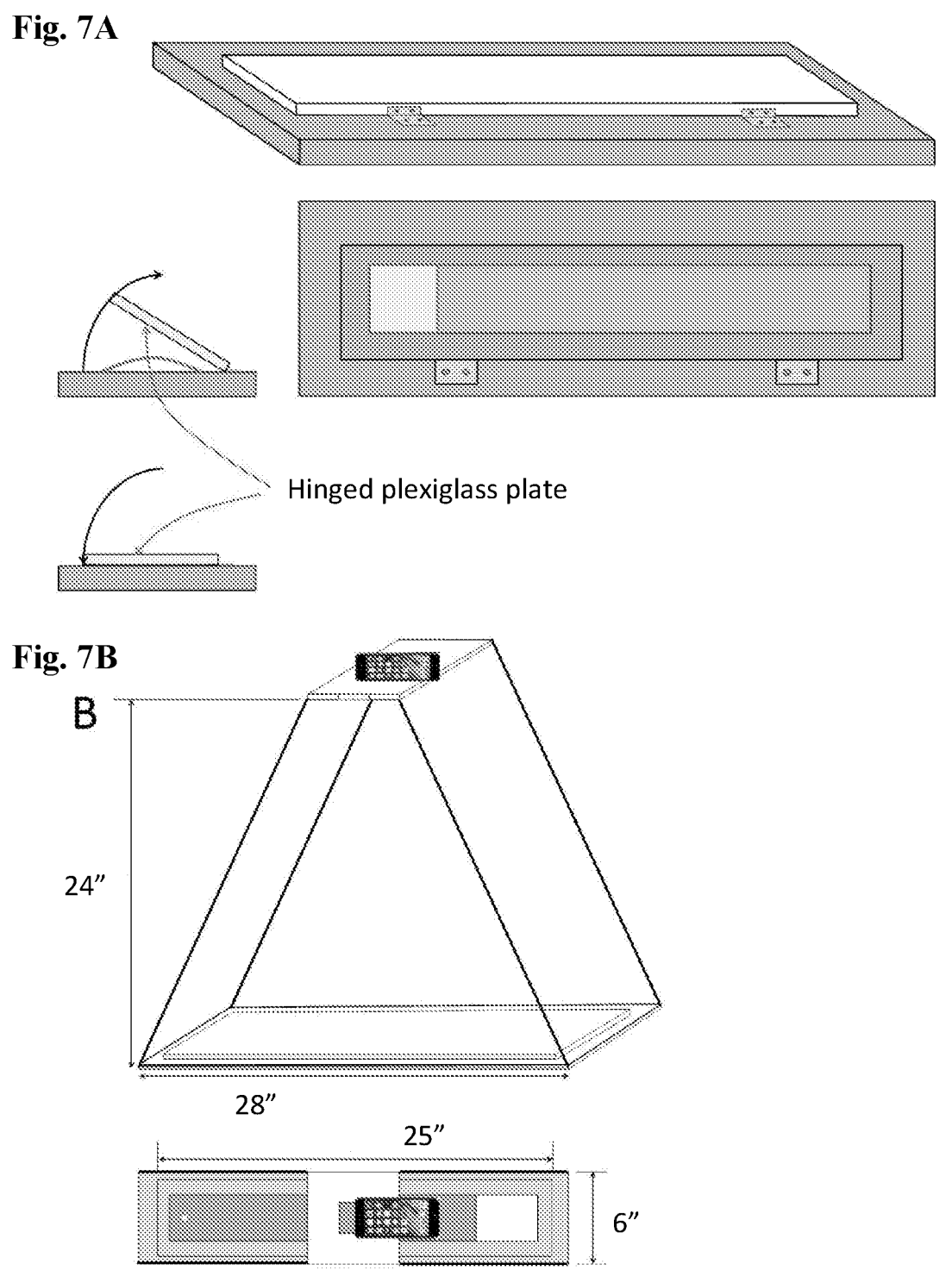

Images of the film may be readily captured, e.g., such as by using a digital camera as noted above. Preferably, the film is unrolled and flattened prior to image capture. A jig or holder may be provided that secures and flattens the plastic film (FIG. 7A). In one embodiment, the holder includes a planar support upon which the film may be disposed. A transparent cover cooperates with the planar support, and is configured to secure and flatten the film when disposed on the planar support. For example, a transparent cover (e.g., formed from plexiglass) may be hingedly connected to the planar support as shown in FIG. 7A. In addition, the holder preferably retains the image capture device at a proper distance from the film to ensure that images of the various films are consistent in size and resolution, and to ensure that the entire film is captured in the image. In one embodiment, an image capture jig is provided which may be disposed above the holder and aligns an image capture device (e.g., a digital camera, such as on a phone) a defined distance therefrom. For example, the jig may include a platform on which an image capture device may be positioned, and support legs extending therefrom and maintaining the platform above the holder as shown in FIG. 7B. As shown in FIG. 7B, the platform has a rectangular configuration with sides of approximately 25 inches by six inches, respectively, and the support legs maintain the platform at a height of about 24 inches above the holder. However, one of skill in the art would readily appreciate that the dimensions referenced in the figure are exemplary only, and may be readily modified as desired and as appropriate for the image capture device utilized, as well as the size and shape of the film or coated substrate being assessed. The holder and/or jig are therefore suitably sized and shaped to ensure that all images of film strips are recorded in a standardized manner. The holder is preferably light weight, and suitable for use in either the field or in the lab.

The computer application (e.g., smartphone application) links any images relating to the particular deployment or retrieval site, and to the particular film at issue. The captured images may be quantified by: a) identifying the boundaries of the image to be analyzed; b) classifying all portions of the image into areas where either the oxide coating or has not been substantially removed; c) quantifying (by number and percentage of pixels) the areas where the oxide coating has been substantially removed, through a vertical gradient along the length of the film strip. The magnitude, distribution and proximity to the soil surface of the removed oxide coating, is assessed to determine whether or not a specified threshold of removal has been exceeded.

Reactive Coating Material

As noted above, the IRIS film may be coated with any sensitive or reactive material. In some embodiments, the film is coated with an iron oxide or mixture of iron oxides, e.g. such as a ferrihydrite-goethite coating as described in U.S. Pat. No. 7,550,297, the disclosure of which is incorporated herein by reference. For example, a formulation of ferrihydrite and goethite in suspension (ranging between 40% and 60% of each) may be utilized, which is readily applied to a PVC device and produces a durable iron oxide coating thereon.

In other embodiments, an IRIS device is provided that includes a reactive coating material comprising a manganese oxide as disclosed herein. In some implementations, the flexible coated plastic film for use in the disclosed IRIS system and methods comprises the Mn oxide coating.

Synthesis of Manganese Oxide Coating

The method of Händel et al. (2013) calls for preparing 0.063 mol solutions of $KMnO_4$ by dissolving each 1.00 g of $KMnO_4$ in 100 mL of deionized (DI) water. For each gram (0.0063 mol) of $KMnO_4$, 1 mL of 50% sodium lactate (0.0056 mol) was added to the $KMnO_4$ solution while stirring using a magnetic stir bar, which is continued for 2 hours. Thus, a sodium lactate/$KMnO_4$ molar ratio of 0.89 was utilized. A series of experiments were run varying the quantity of the reducing agent (sodium lactate) such that the sodium lactate/$KMnO_4$ ratios spanned an order of magnitude and ranged from 0.89 to 11.1.

In a first experiment, four solutions were each prepared by dissolving 10 g (0.0633 mol) of $KMnO_4$ in 1 l of DI water. To these four solutions were added 8, 10, 12, or 20 mL of 60% sodium lactate solution, resulting in molar ratios (sodium lactate/$KMnO_4$) of 0.89, 1.12, 1.34, and 2.23, respectively. All batches were stirred continuously for 2 hours, after which they were allowed approximately 45 min for the newly synthesized manganese oxide to flocculate and settle. The materials were transferred to 250-mL centrifuge bottles, where they were centrifuge washed (1500 rpm for 5 min) three to four times with DI water until the flocculated manganese oxide began to disperse. After the first slightly cloudy supernatant was discarded, the cake (remaining solids) of manganese oxide was thoroughly resuspended in DI water and transferred to cellulose dialysis tubing with a molecular weight cutoff of 12,000 to 14,000; the sections of tubing were placed in basins (approximately 6 L) of DI water. The DI water was changed at roughly 12-hour intervals during the course of 3 days. After 3 days, the manganese-oxide suspensions were then transferred from the dialysis tubing to NALGENE® bottles, where the materials were thoroughly homogenized by shaking, and all samples were adjusted to the same final volume (375 mL) by adding DI water. Triplicate 1-mL aliquots of each of the four suspensions were transferred to weighed Al pans and dried at 105° C. to estimate the concentration of the suspensions and the total mass of manganese oxides synthesized in each treatment.

On the day they emerged from dialysis, a 25-mL volume of each suspension was transferred to a weighed 40-mL polycarbonate centrifuge tube and centrifuged at approximately 10,000×g for 15 min and then decanted. The tubes containing the manganese-oxide "cakes" were weighed moist and then after drying at 105° C. The volume of the moist "cake" was estimated from the water volume and the mass and density of the manganese-oxide solids. The same procedure was performed 34 days later, during which intervening time the suspensions were stored at room temperature on the laboratory bench.

Additional sets of manganese oxides were synthesized during the course of several months using various molar ratios of sodium lactate to $KMnO_4$. In these experiments, either 2.00 or 3.00 g of $KMnO_4$ was dissolved in sufficient DI water to make a 0.063 M solution. Sodium lactate solution (60%) was added to the $KMnO_4$ solutions using volume (mL) to mass (g) ratios of 0.8, 1, 1.2 2, 3, 4, 6, and 10, which achieved molar ratios (sodium lactate/$KMnO_4$) of 0.89, 1.11, 1.33, 2.22, 3.33, 4.43, 6.65, and 11.1, respectively. Synthesis, centrifugation, and dialysis were performed as described above.

The suitability of these various manganese oxides as paints for making manganese oxide coated IRIS tubes was evaluated by centrifuging (to remove excess water) or adding DI water so that the consistency of the suspension was about equal to that of heavy cream or thin yogurt. While a thinner, less viscous iron paint is acceptable for manufacturing iron-coated IRIS tubes, manganese-oxide suspensions that were less viscous than prescribed herein resulted in insufficient pigment on the substrate and/or resulted in a coating having a relatively light or pale color. To reach the desired viscosity, 50 mL of the proper manganese-oxide suspension was centrifuged in a 100-mL Nalgene centrifuge tube at 2000 rpm (~1000 G) for 5 min, decanting and discarding the supernatant, and then loosening and homogenizing the cake in the tube using a vortex mixer without adding additional water.

The resulting "thick suspension" or "paint" was then applied to a lightly sanded (300 grit) PVC tube (½ inch schedule 40, 21.3-mm OD) using a foam brush while the tube was rotated (~100 rpm) in a lathe-type device, much like the application of iron paint has previously been described (Jenkinson, B and Franzmeier, D. (2006) "*Development and evaluation of Fe coated tubes that indicate reduction in soils*," Soil Sci. Soc. Am. J. 70:183-191; Rabenhorst, M and Burch, S. (2006) "*Synthetic iron oxides as an Indicator of Reduction in Soils (IRIS)*," Soil Sci. Soc. Am. J. 70:1227-1236). After the paint had dried, the durability of the paint was evaluated by rubbing a finger along the painted tube, as described by Rabenhorst, M and Burch, S. (2006) "*Synthetic iron oxides as an Indicator of Reduction in Soils (IRIS)*," Soil Sci. Soc. Am. J. 70:1227-1236, and using the following numerical scale from 1 to 5:1—paint wipes off when applying very slight pressure; 2—paint wipes off when applying slight pressure; 3—paint wipes off when applying moderate pressure; 4—paint wipes off only when applying firm pressure; 5—paint does not wipe off when applying firm pressure.

The mineralogical characteristics of the manganese oxides were examined using X-ray diffraction. Samples of the manganese-oxide suspensions were freeze-dried before examination. X-ray diffraction scans were collected on randomly oriented powder mounts using a PANALYTICAL® PW1830 X-ray diffractometer equipped with a Cu tube and a curved crystal graphite monochrometer. Samples were scanned from 4 to 80° 2θ at a rate of 0.60° 2θ min$^{-1}$.

Function of Manganese-Coated Device

To evaluate the function of manganese oxide coated tubes relative to iron-coated tubes, manganese oxide coated tubes were prepared by painting lightly sanded PVC tubes (0.5 inch schedule 40) with manganese oxides synthesized using a sodium lactate/KMnO$_4$ ratio of 6.7. Tubes were also painted with iron oxides synthesized according to the procedure of Rabenhorst, M and Burch, S. (2006) "*Synthetic iron oxides as an Indicator of Reduction in Soils (IRIS)*," Soil Sci. Soc. Am. J. 70:1227-1236, and ensuring that the ferrihydrite-goethite suspension contained between 40 and 60% goethite so that the iron oxides would adhere well to the tubes. Thirty tubes of each type (Mn and Fe) were installed in a soil (a Typic Fluvaquent) in a forested discharge wetland along Indian Creek, Maryland (39.028580, −76.841320) that was similar to the Zekiah soil series. Each tube was inserted into a pilot hole made using a 22-mm-diameter push probe (Rabenhorst, M. (2008) "*Protocol for using and interpreting IRIS tubes*," Soil Surv. Horiz. 49:74-77). A recording temperature probe was installed at a depth of 25 cm and measurements were recorded hourly. Redox potentials were measured at weekly intervals at depths of 10, 25, and 40 cm using eight replicate Pt electrodes and a high-resistance volt meter (Rabenhorst, M. (2009) "Making soil oxidation-reduction potential measurements using multimeters," Soil Sci. Soc. Am. J. 73:2198-2201; Rabenhorst et al. (2009) "*Measurements of soil redox potential*," Soil Sci. Soc. Am. J. 73:668-674), and pH measurements (approximately 1:1 soil/water paste) were made on soil materials collected from depths of 10, 25, and 40 cm on each day that redox measurements were made. Five manganese oxide coated tubes and five iron-coated tubes were removed after 2, 4, 7, 14, 21, and 28 days. The tubes were returned to the laboratory, where they were gently washed to remove adhering soil, and then both sides of the tubes were photographed. The quantity of paint removed was estimated using grid counting techniques (Rabenhorst, M. (2012) "Simple and reliable approach for quantifying IRIS tube data," Soil Sci. Soc. Am. J. 76:307-308).

Results and Discussion

Figure 8:
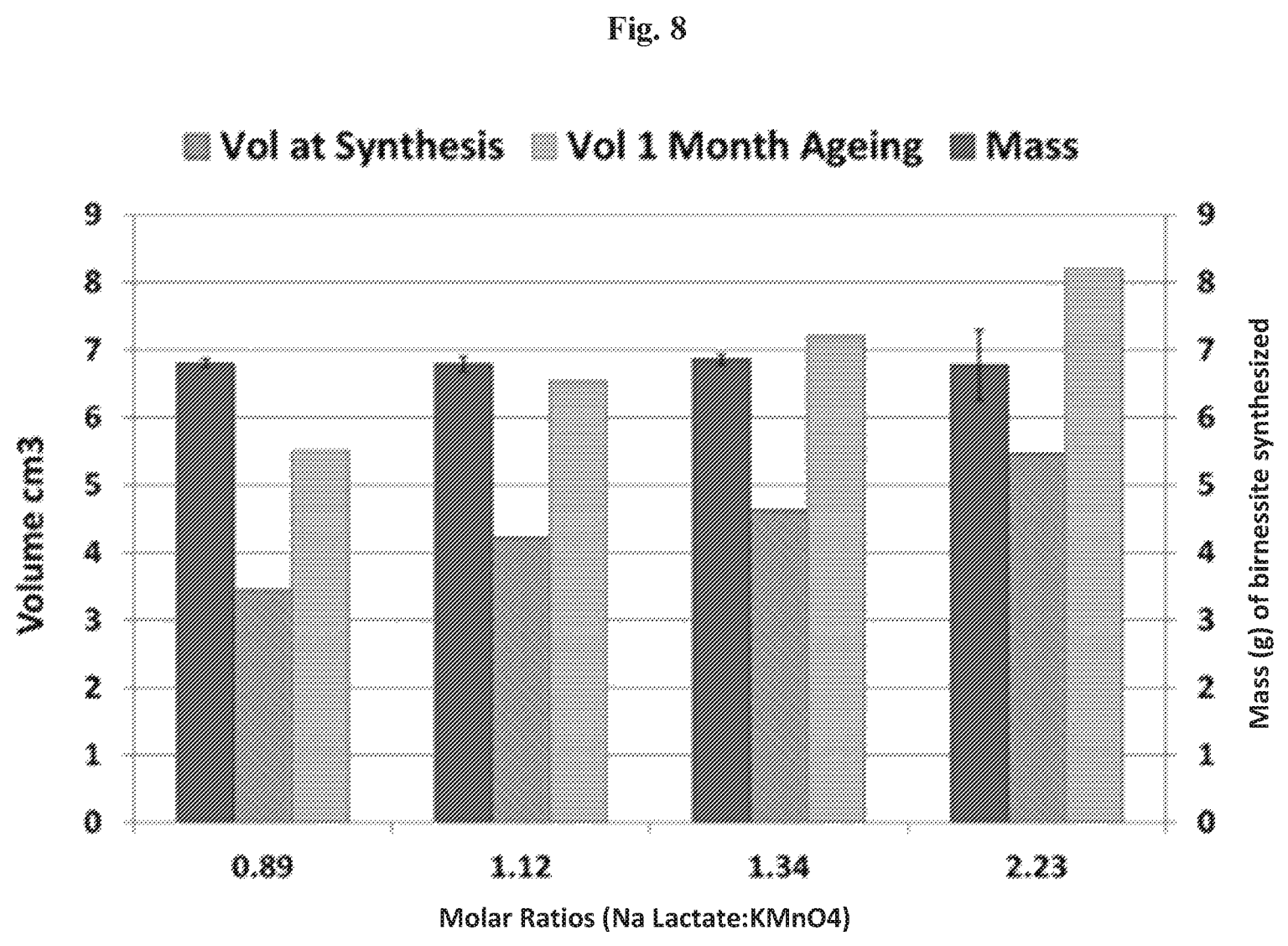

During the initial synthesis experiment, the colors of the KMnO$_4$ solutions changed from deep purple to black, and this change occurred more rapidly when higher sodium lactate ratios were used. In this process, Mn$^{7+}$ in the KMnO$_4$ is reduced to Mn$^{3+}$ or Mn$^{4+}$, which precipitates as birnessite, while the lactate is oxidized, presumably to pyruvate or oxalate. The same mass of manganese oxide was formed regardless of the sodium lactate/KMnO$_4$ ratio (0.9, 1.1, 1.3, or 2.2) used (FIG. 8), which indicated that the formation of manganese oxides was not limited by the quantity of sodium lactate used. Based on the formula for birnessite [(Na,K)$_{0.5}$ (Mn$^{4+}$,Mn$^{3+}$)$_2$O$_4$·1.5H$_2$O], all four syntheses resulted in the formation and recovery of >99% of the predicted mass of manganese oxide. It was noted, however, that the volumes of the centrifuged samples increased markedly as the sodium lactate to KMnO$_4$ ratio was increased (FIG. 8). This occurred both at the time the samples were initially removed from dialysis, and also when they were examined 34 days later (when all volumes had increased). This indicates that a greater degree of polymerization of the manganese oxides was facilitated by the sodium lactate, induced by more rapid initial precipitation of the oxides.

Figure 9:
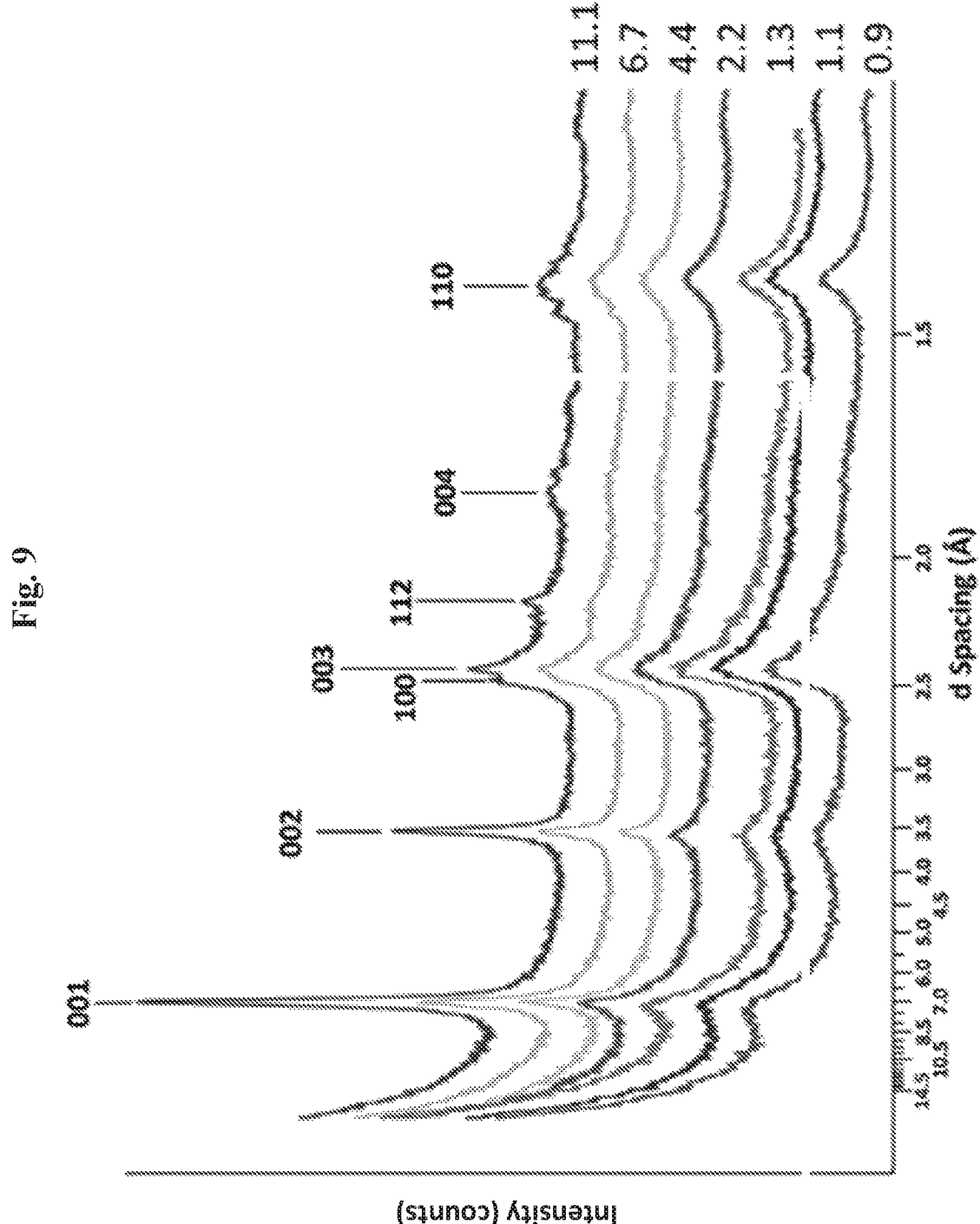
FIG. 9 shows X-ray diffraction patterns for manganese oxides synthesized using Na lactate to K permanganate ($KMnO_4$) ratios ranging from 0.9 to 11.1. Synthesis using higher ratios caused the birnessite to be much more crystalline, as shown by sharper and more numerous peaks.
Figure 10:
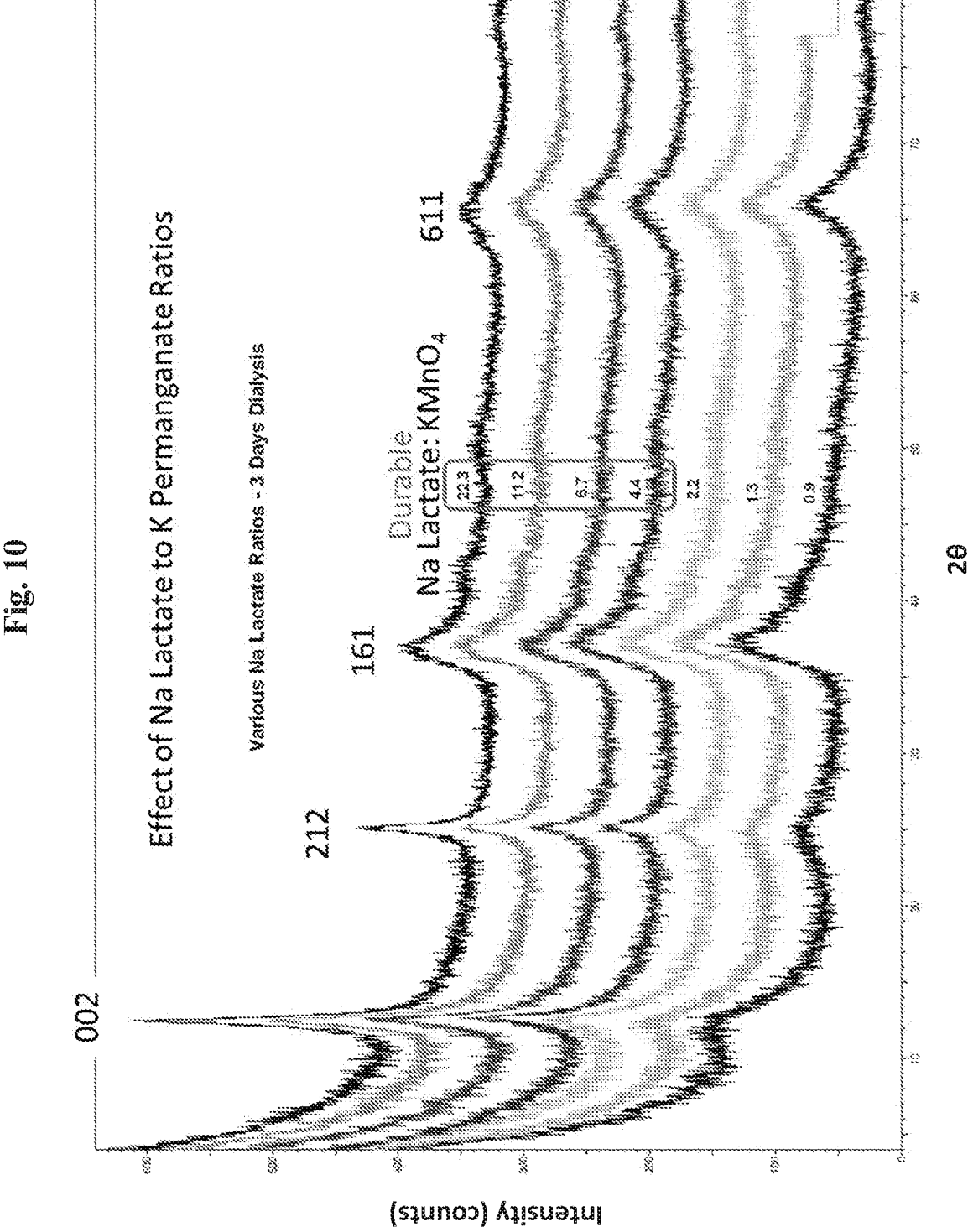
FIG. 10 shows X-ray diffraction patterns for manganese oxides synthesized (2 hour reaction followed by 3 days of dialysis) by reducing 0.063 M $KMnO_4$ with Na lactate, with Na lactate to $KMnO_4$ ratios ranging from 0.9 to 22.3. As $KMnO_4$ molar ratio increased, the birnessite became more crystalline as evidenced by sharper peaks (002 and 212). Crystalline birnessite formed at ratios of 4.4 or higher exhibited excellent durability as a manganese oxide coating when painted onto a lightly sanded PVC device, whereas birnessite formed at ratios between 0.9 and 2.2 exhibited poor durability on a comparable PVC device and rubbed off easily.

Analysis by X-ray diffraction indicated that the manganese oxide formed was birnessite, although the degree of crystallinity changed markedly as the sodium lactate/ KMnO$_4$ ratio during synthesis changed (as compared to Händel et al. (2013) "*A simple method to synthesize birnessite at ambient pressure and temperature*," Geoderma 193-194:117-121). When a molar ratio of 0.9 was used (e.g., as provided in the method of Händel et al., 2013), a very poorly crystalline birnessite was formed that showed only four very broad peaks (001, 002, 100, and 110) (FIG. 9). However, as the sodium lactate/KMnO$_4$ ratio was increased, the X-ray patterns showed increasingly sharp birnessite peaks (for two of the initial four peaks observed) and also the emergence of a number of additional peaks, such that by the time the sodium lactate/KMnO$_4$ ratio reached 11, at least three additional birnessite peaks could be seen (003, 112, and 004) (FIG. 9 and FIG. 10).

Figure 12:
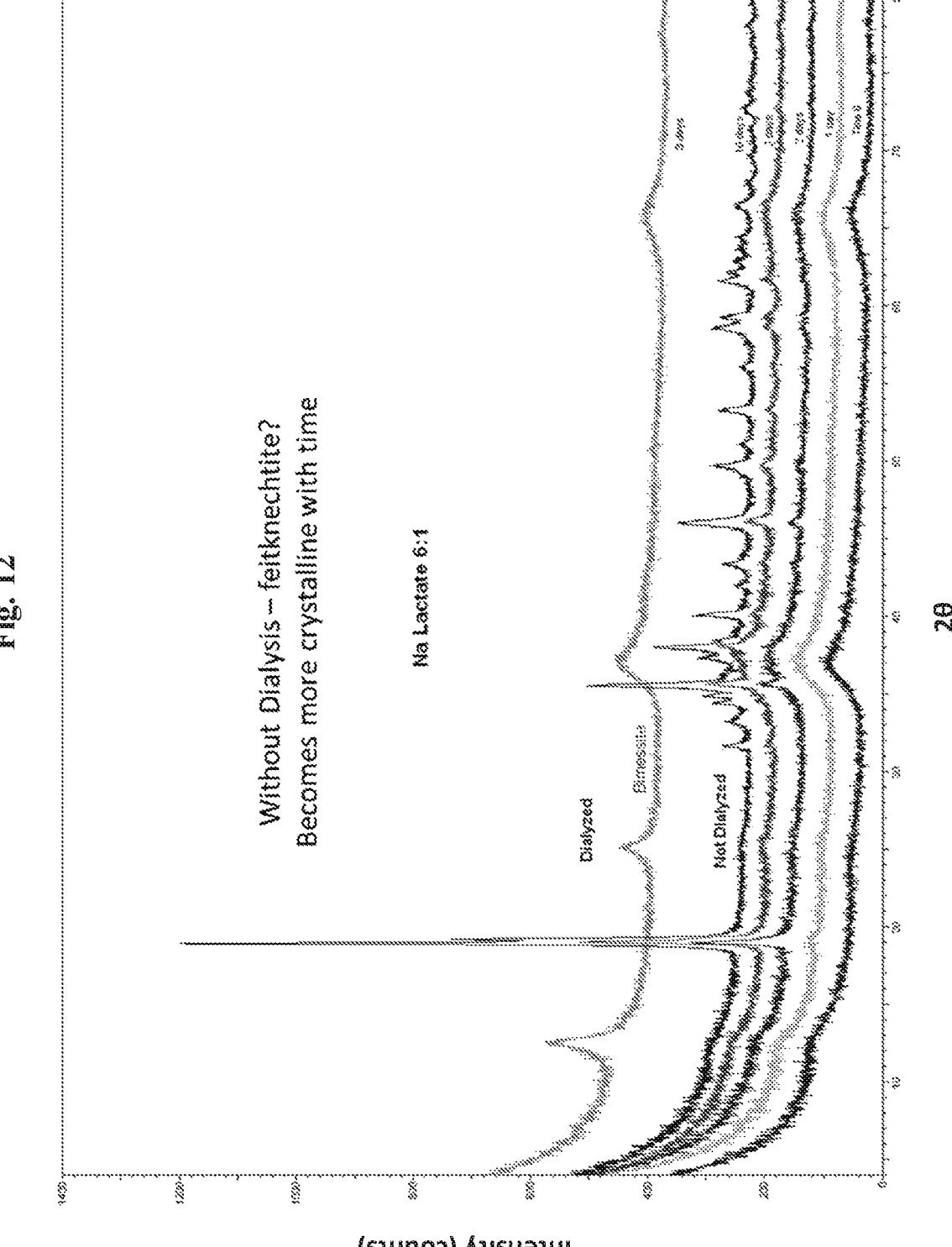
FIG. 12 illustrates the effect of not removing excess reagents with centrifugation and dialysis of manganese oxide synthesized by reducing 0.063 M $KMnO_4$ with Na lactate to $KMnO_4$ ratio of 6.7, showing the formation of feitknechtite ($\beta$-$Mn^{3+}O(OH)$) when excess reagents (particularly reducing agent Na lactate) is not removed via centrifugation and dialysis, whereas birnessite is formed when the materials are centrifuged and dialyzed.

In addition, X-ray diffraction patterns showed a change in crystallinity of birnessite with additional aging. Increased crystallinity of birnessite synthesized (2-hour reaction followed by 3 days of dialysis) by reducing 0.063 M KMnO$_4$ with Na lactate to KMnO$_4$ ratio of 6.7 was observed between the period of initial synthesis, the 3 days of dialysis, and subsequent sample storage (FIG. 11). Note that the elimination of centrifugation and dialysis steps resulted in the formation of feitknechtite ($\beta$-$Mn^{3+}O(OH)$), wherein excess reagents (particularly reducing agent Na lactate) were not removed (FIG. 12).

Figure 13:
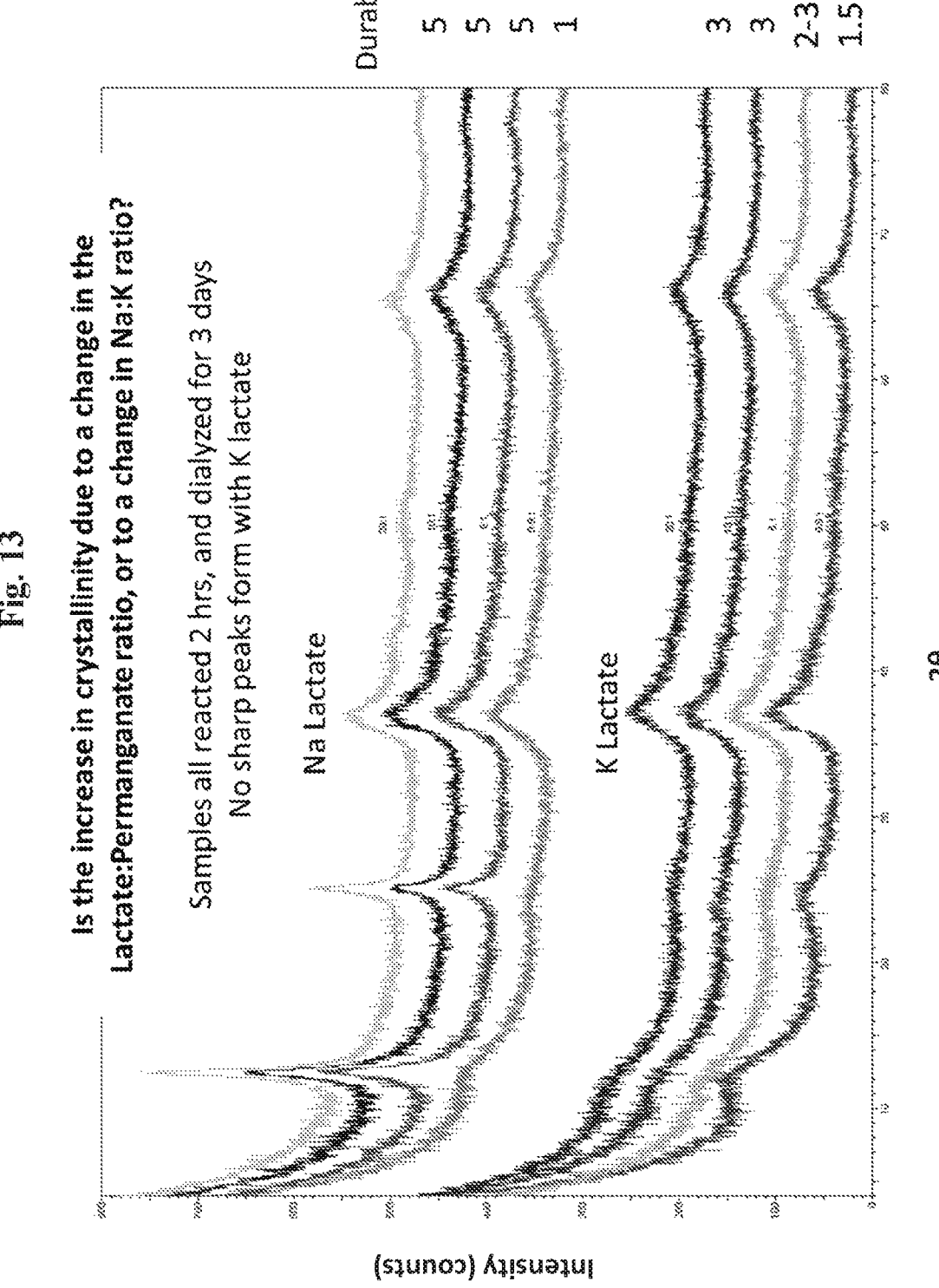
FIG. 13 illustrates X-ray diffraction patterns for manganese oxides synthesized (2 hour reaction followed by 3 days of dialysis) by reducing 0.063 M $KMnO_4$ solutions with either Na lactate or K lactate, with molar ratios of lactate to permanganate ranging between 0.9 and 22. Whereas higher molar ratios of Na lactate (6.7 and higher) resulted in increased crystalline birnessite (evidenced by much sharper 002 and 212 peaks), the birnessite formed using K lactate did not become crystalline. In addition, all of the more crystalline birnessites formed using Na lactate exhibited excellent durability when painted on PVC tubes. In contrast, the more poorly crystalline birnessites that were formed using K lactate exhibited poor durability when painted on PVC tubes.

In order to confirm that the increase in crystallinity of the birnessite was due to the change in Na lactate to permanganate ratio, as opposed to a change in Na lactate to K ratio, testing of $KMnO_4$ reduced with Na lactate versus K lactate was conducted. Mn oxides synthesized by reducing 0.063 M $KMnO_4$ solutions with either Na lactate or K lactate, with molar ratios of lactate to permanganate ranging between 0.9 and 22. Higher molar ratios of Na lactate (6.7 and higher) resulted in increased crystalline birnessite, as evidenced by much sharper 002 and 212 peaks (FIG. 13). In contrast, birnessite formed using K lactate did not become as crystalline. In addition, all of the more crystalline birnessites formed using Na lactate exhibited excellent durability when painted on PVC tubes, whereas the more poorly crystalline birnessites that were formed using K lactate exhibited poor durability when painted on PVC tubes.

Figure 14:
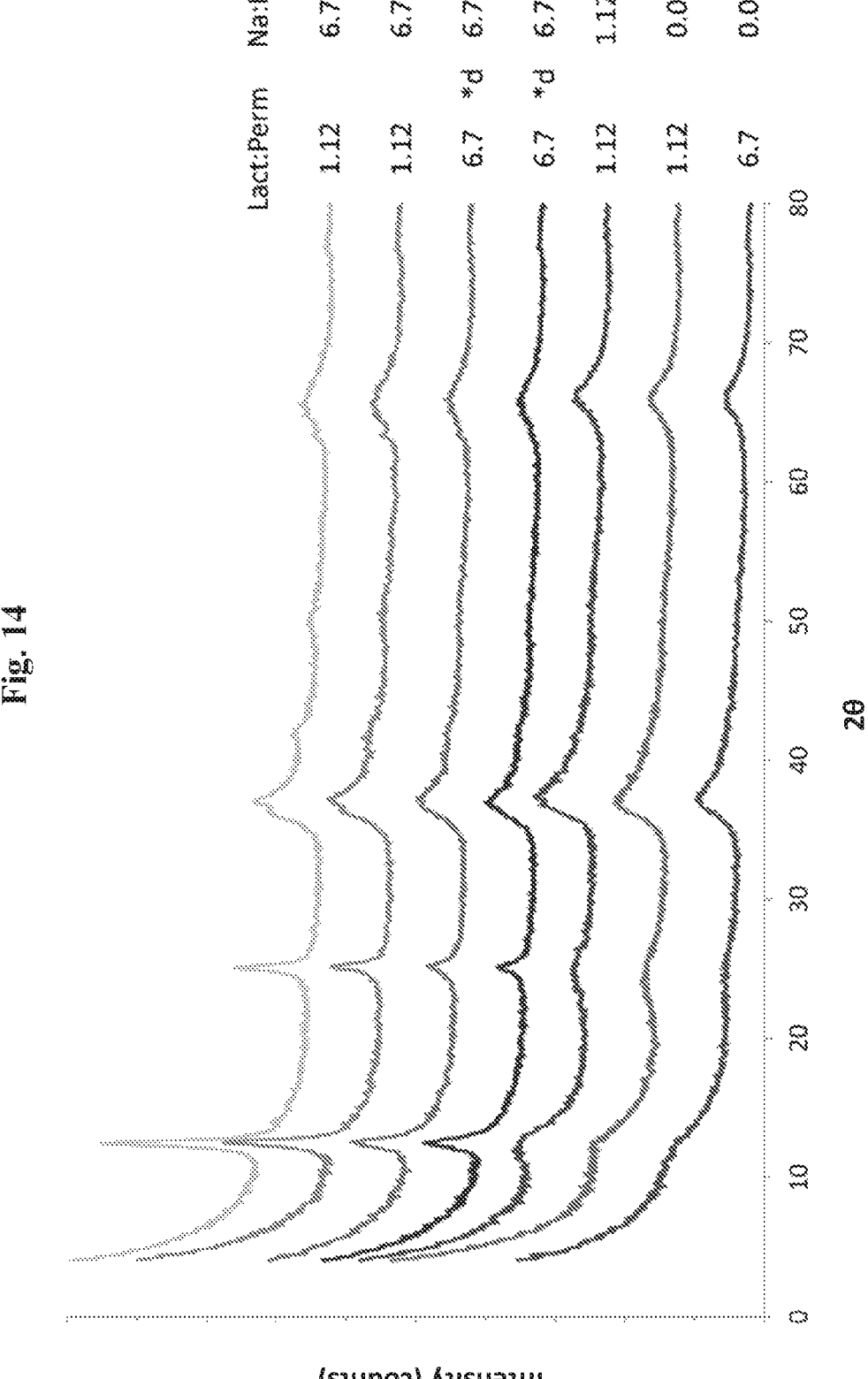
FIG. 14 illustrates X-ray diffraction patterns for Mn oxides synthesized under conditions where the lactate to permanganate ratios were manipulated to be either 1.1 or 6.7, and the Na to K ratios were 6.7, 1.1 or 0.0. The ratios were adjusted independently by using either Na lactate or K lactate to reduce $KMnO_4$ solutions, and by adding NaCl in some instances to enhance the Na:K ratios. The strongest peaks (002 and 212) for birnessite were observed when the Na:K ratio was high (6.7) and the lactate:permanganate ratio was low (1.1). When the Na:K ratio was low (1.1 or below), very poorly crystalline birnessite was formed, regardless of whether the lactate:permanganate ratio was low (1.1) or high (6.7). When the lactate:permanganate ratios and the Na:K ratios were both high (6.7), a crystalline birnessite was formed (regardless of whether this was done using Na lactate or using K lactate with NaCl added), although the peaks (002 and 212) were not as strong or sharp as when Na:K ratio was high and lactate:permanganate was low. Only those birnessites synthesized under high Na:K ratio (6.7) and high lactate:permanganate ratio (6.7) produced a highly durable manganese oxide coating (*d in FIG. 14) when painted onto PVC tubes. Surprisingly, the more crystalline birnessites formed under high Na:K and low lactate: permanganate ratios formed coatings on PVC tubes that had very poor durability and rubbed off easily.

X-ray diffraction patterns for Mn oxides synthesized under conditions where the lactate to permanganate ratios were manipulated to be either 1.1 or 6.7, and the Na to K ratios were 6.7, 1.1 or 0.0, were tested (FIG. 14). The ratios were adjusted independently by using either Na lactate or K lactate to reduce $KMnO_4$ solutions, and by adding NaCl in some instances to enhance the Na:K ratios. The strongest peaks (002 and 212) for birnessite were observed when the Na:K ratio was high (6.7) and the lactate:permanganate ratio was low (1.1). When the Na:K ratio was low (1.1 or below), very poorly crystalline birnessite was formed, regardless of whether the lactate:permanganate ratio was low (1.1) or high (6.7). When the lactate:permanganate ratios and the Na:K ratios were both high (6.7), a crystalline birnessite was formed (regardless of whether this was done using Na lactate or using K lactate with NaCl added), although the peaks (002 and 212) were not as strong or sharp as when Na:K ratio was high and lactate:permanganate was low. Only those birnessite synthesized under high Na:K ratio (6.7) and high lactate:permanganate ratio (6.7) produced a highly durable Mn oxide coating (*d in FIG. 14) when painted onto PVC tubes. Surprisingly, the more crystalline birnessites formed under high Na:K and low lactate:permanganate ratios formed coatings on PVC tubes that had very poor durability and rubbed off easily.

Figure 15:
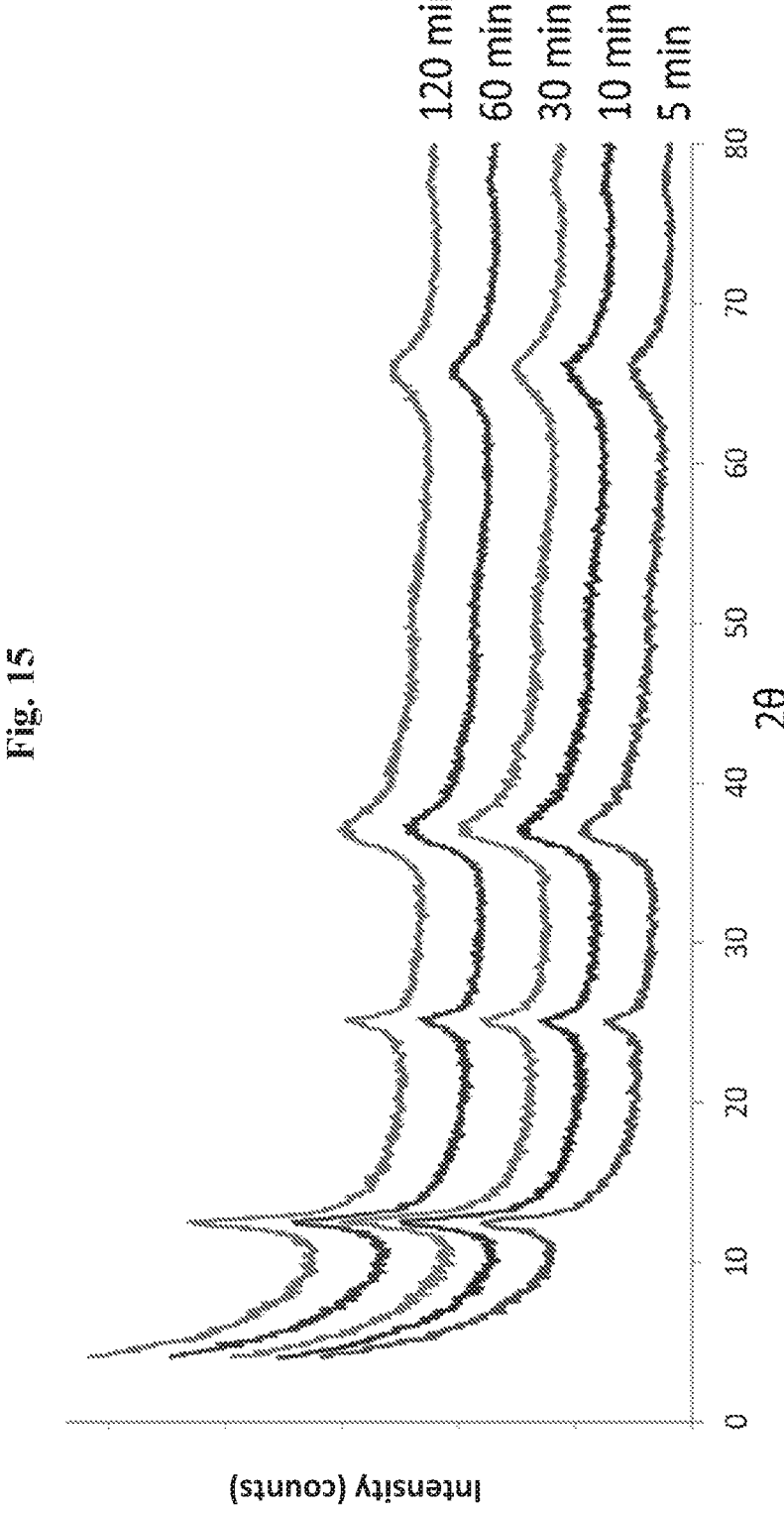
FIG. 15 illustrates X ray diffraction patterns for manganese oxides synthesized by reducing 0.063 M $KMnO_4$ solutions with Na lactate at a molar ratio of Na lactate to permanganate of 6.7 for various lengths of time ranging from 5 to 120 minutes. At the end of the reaction period, each sample was centrifuge washed in DI water (1500 rpm for 3 min) three times in quick succession and then transferred to dialysis tubing and dialyzed for 3 days (DI water changed every 12 hours). The intensity of the peaks (002 and 212) for the 5 minute sample was slightly smaller than other samples. However, generally very little difference was observed between the samples, indicating that an increase in the length of reaction time from 10 to 120 minutes has little impact on the crystallinity of the birnessite formed.

The effect of reaction time when reducing $KMnO_4$ using Na lactate was evaluated. Manganese oxides were synthesized by reducing 0.063 M $KMnO_4$ solutions with Na lactate at a molar ratio of Na lactate to permanganate of 6.7 for various lengths of time ranging from 5 to 120 minutes. At the end of the reaction period, each sample was centrifuge washed in DI water (1500 rpm for 3 min) three times in quick succession and then transferred to dialysis tubing and dialyzed for 3 days (DI water changed every 12 hours). The intensity of the peaks (002 and 212) for the 5-minute sample was slightly smaller than other samples. However, generally very little difference was observed between the samples, indicating that an increase in the length of reaction time from 10 to 120 minutes has little impact on the crystallinity of the birnessite formed (FIG. 15).

Figure 16:
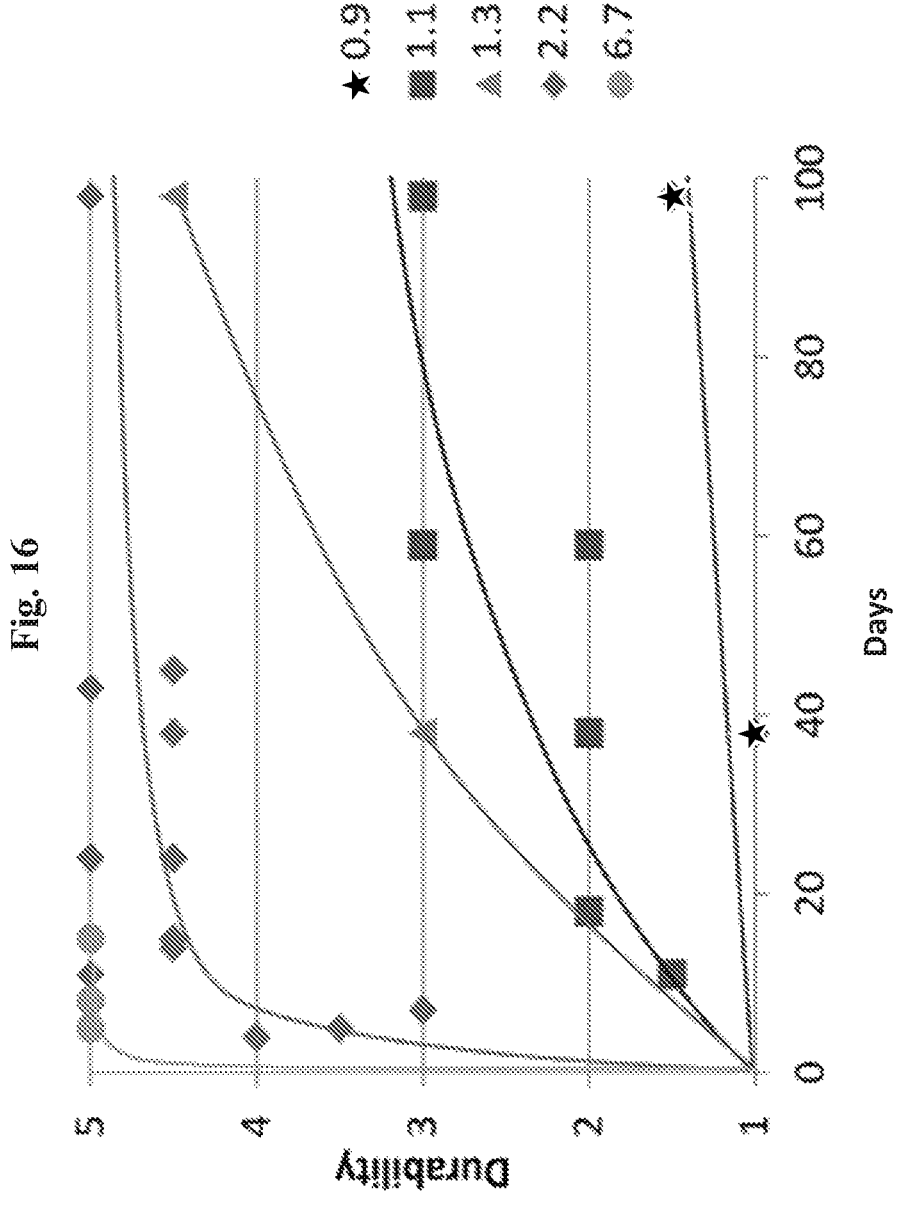
FIG. 16 illustrates durability of manganese-oxide paints synthesized using various Na lactate to $KMnO_4$ ratios (0.9, 1.1, 1.2, 2.2, 6.7) when applied to lightly sanded PVC tubes using a lathe-type device. Molar ratios of 6 or above consistently produced materials that, immediately after 3 days of dialysis, showed high durability (5 on the 1-5 scale proposed by Rabenhorst, M and Burch, S. (2006) "*Synthetic iron oxides as an Indicator of Reduction in Soils (IRIS)*," Soil Sci. Soc. Am. J. 70:1227-1236).

By applying the Mn oxides to pre-sanded PVC tubes using a lathe device, approximately 30 tubes 60 cm in length (50 cm of painted length) could be prepared in about 1 hour. Birnessite that was synthesized according to the formulation of Händel et al. (2013) always showed very poor adhesion and durability (1 or 2 on the evaluation scale), and all oxides that were synthesized at ratios<2 never achieved a satisfactory durability even if the oxides were permitted to age up to 100 days (FIG. 16). Oxides synthesized with a ratio of approximately 2 showed mixed results. Sometimes within a few weeks, they would show a relatively good adherence to the PVC tubes and good durability, but other times they would not. However, when the oxides were synthesized using a ratio of 6 or more, they consistently and immediately (after 3 days of dialysis) showed excellent adhesion to the PVC tubes and also showed excellent durability (5 on the evaluation scale).

Figure 17:
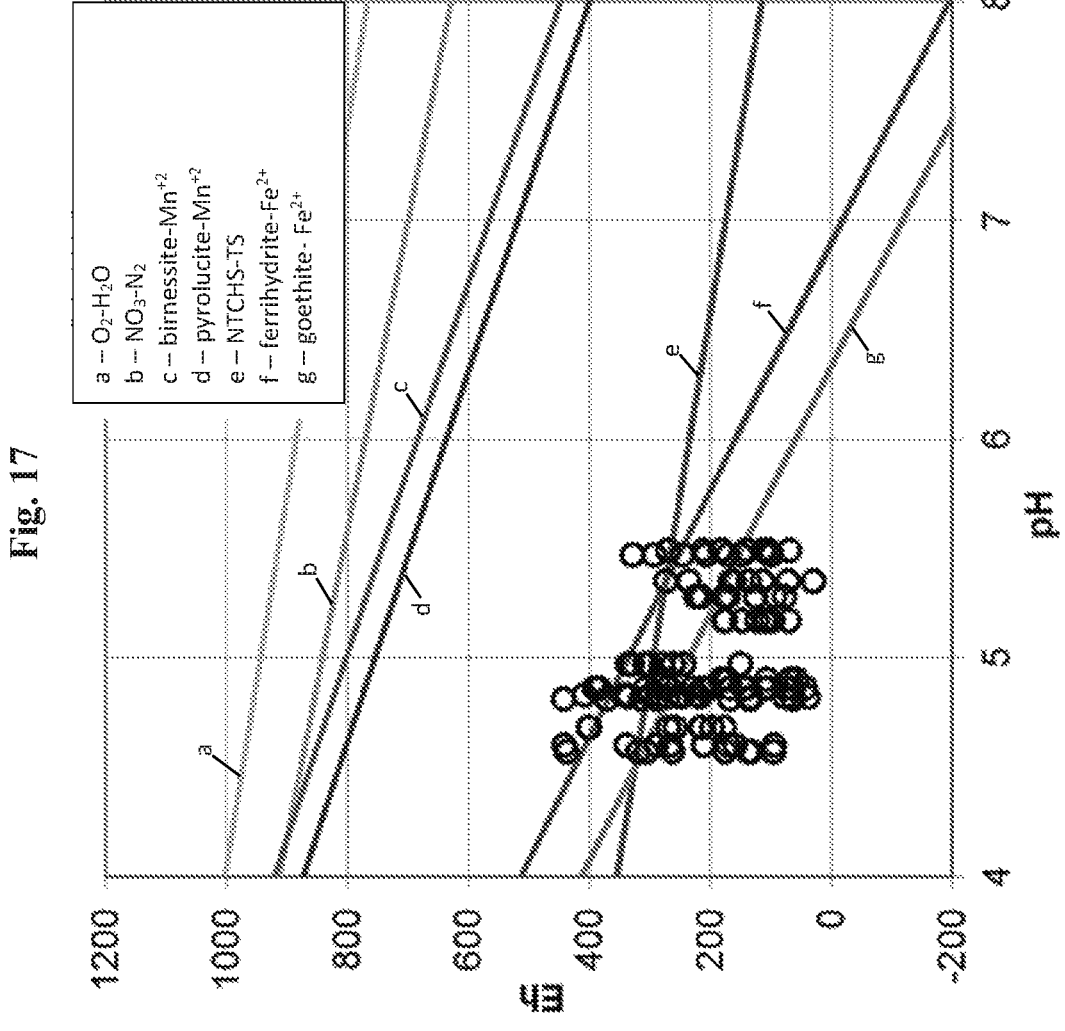
FIG. 17 illustrates redox potential (Eh) and pH measured at the field site during the 28-day period when iron oxide and manganese oxide coated IRIS tubes were installed. All the points plot below the manganese-oxide lines, and the vast majority plot below the iron oxide lines, indicating that the soil conditions were strongly reducing.

The soil at the study site remained essentially saturated to the surface for the entire 28 days (21 April-19 May) that the tubes were installed. The soil temperature at 25 cm ranged between 10.4 and 16.7° C., and the average temperature during the 28 days was 13.7° C. The plot of Eh and pH data did not differ significantly with depth and did not show any particular trend with time, so the data were plotted together (FIG. 17). All of the plotted data points are located well below the lines for the Mn oxides (pyrolucite and birnessite). With regard to iron oxides, 93% of the observations are below the ferrihydrite stability line and 65% are below the goethite line. 85% of the data also fall below the technical standard line from the NTCHS (National Technical Committee for Hydric Soils (2007) Technical standards for hydric soils, Tech. Note 11. NRCS, Washington, DC.). As evident from the data, the soil was strongly reducing during the period when the tubes were installed.

Figure 18:
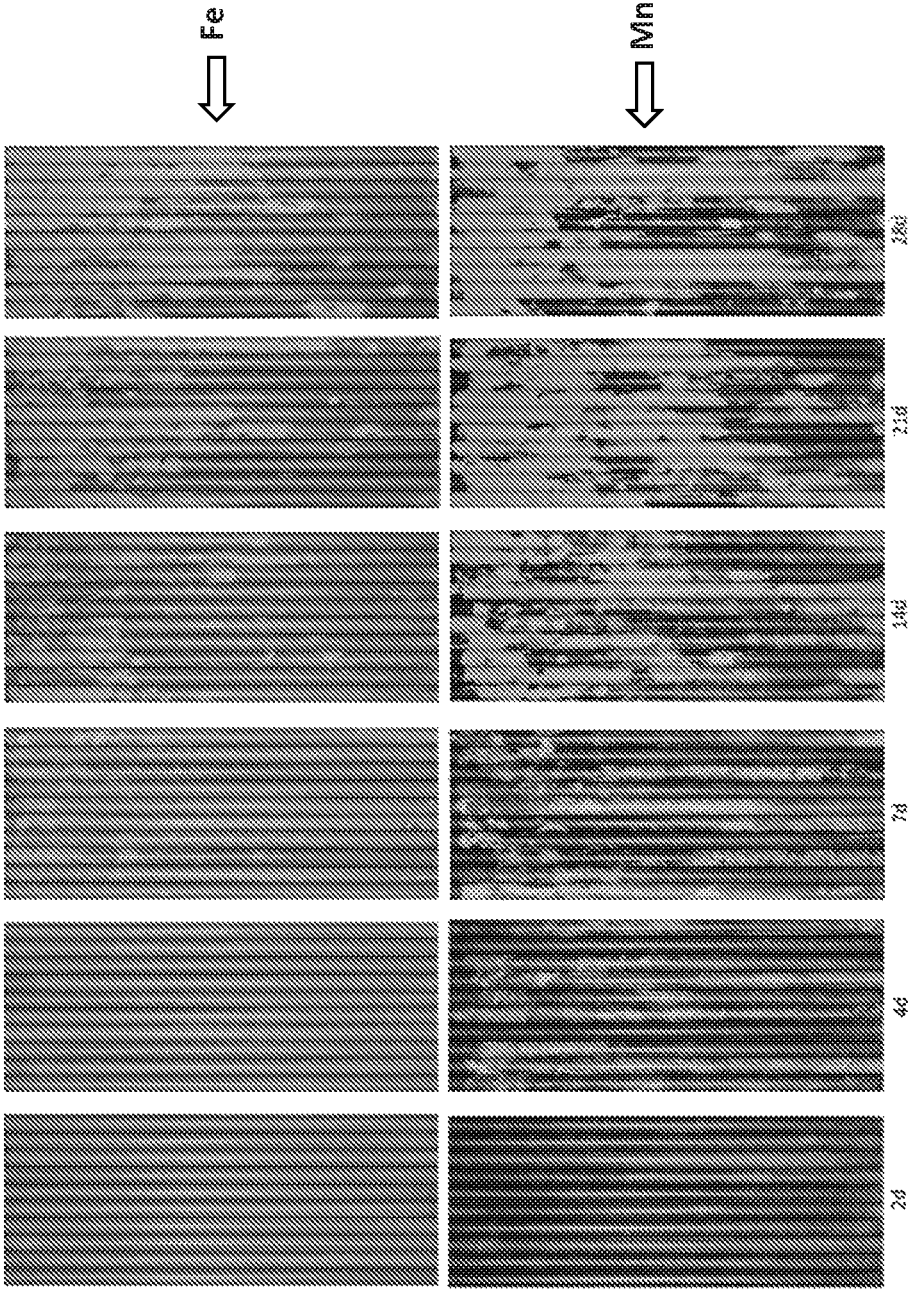
FIG. 18 are images of IRIS tubes coated with Fe oxides (top panels) and Mn oxides (bottom panels) that had been installed in a strongly reducing soil in a forested discharge wetland and were extracted 2, 4, 7, 14, 21, and 28 days after installation. Each image represents the front and rear of five replicated tubes that were approximately 50 cm in length. The top of each image represents the level of the soil surface.
Figure 19:
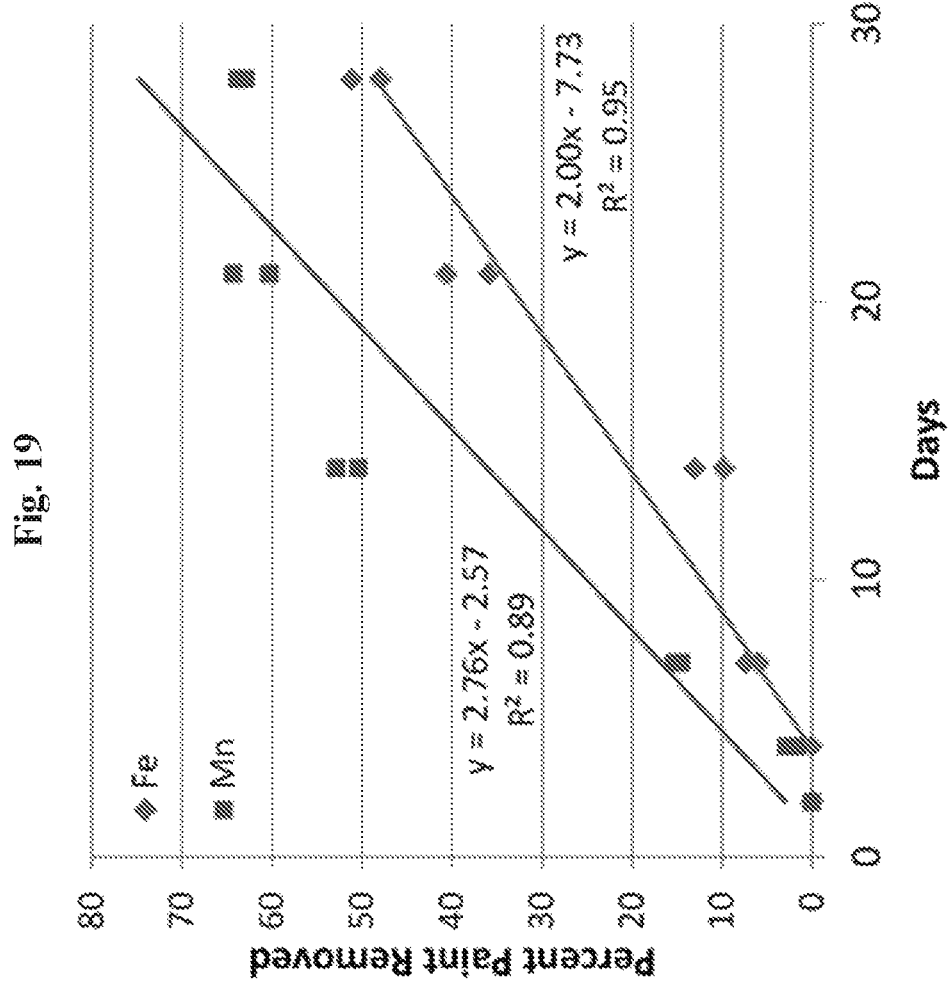
FIG. 19 shows percentage of iron and manganese paint removed with time from IRIS tubes installed in a wetland soil for 28 days. Comparisons of the two regressions indicates that there is a significant difference between the two lines (p=0.0003).

Images of the IRIS tubes extracted from the wetland were obtained (FIG. 18), and the percentage of paint removed with time shown (FIG. 19). Both the percentage of iron paint removed and the percentage of Mn paint removed are directly related to the length of time the tubes were installed in the wetland (p<0.0001 in both cases). These data also demonstrate, as is also readily visible from the images, that there was significantly more Mn paint than Fe paint removed at any point in time (p=0.0003). Based on the slopes of the two lines, the rate of Mn paint removal (2.76% $d^{-1}$) was approximately 38% greater than that for Fe paint removal (2.00% $d^{-1}$), such that after 28 days, approximately 65% of the Mn paint had been removed while only 50% of the Fe paint had been removed. The magnitudes of paint removal for both types of tubes were well above the 30% threshold suggested by the NTCHS (National Technical Committee for Hydric Soils (2007) Technical standards for hydric soils, Tech. Note 11. NRCS, Washington, DC.). Paint removal from the Mn tubes would have crossed this 30% threshold between 7 and 14 days, whereas paint removal from the Fe oxide coated tubes would have crossed this threshold at approximately 3 weeks. Note that these are conservative estimates given the data in this study were calculated based on the entire 50-cm tube length, whereas the National Technical Committee standard stipulates using the 15-cm zone of maximum paint removal within the upper 30 cm of the tube (which would have been even larger).

This greater removal of Mn paint relative to Fe paint, and the faster rate at which Mn paint is removed relative to Fe paint, are not surprising since the thermodynamic parameters (reflected in the Eh-pH diagrams) predict that Mn oxides should become reduced sooner in wetland soils and because all of the Eh-pH data collected during this trial occurred very much below the Mn oxide stability lines.

By substantially modifying the Händel et al. (2013) method for synthesizing birnessite with 7.5 times increase in the proportion of sodium lactate reductant (resulting in a sodium lactate/$KMnO_4$ molar ratio of 6.7 rather than 0.89) followed by centrifuge washing and dialyzing for 3 days, a much more crystalline birnessite was achieved. This birnessite can be applied quickly and easily to a PVC substrate (e.g., tubing or film material), for example using a brush to produce an IRIS device having a durable Mn oxide coating. This represents a dramatic improvement in the ease by which Mn oxide coated devices can be prepared. For example, using the disclosed methods, approximately 30 tubes can be painted in 1 hour.

The resulting Mn-coated IRIS devices may be used in the field to assess reducing conditions in soils, similar to the way that Fe-coated tubes are used. In a field test, the birnessite coatings of the present invention were reduced and stripped from PVC tubes approximately 40% faster than Fe-oxide coatings were removed. This is reasonable and expected given Mn oxides generally reduce at lower redox potentials as compared to Fe oxides. Thus, birnessite-coated tubes are useful in recognizing anaerobic soil conditions that are less strongly reducing than those required to strip paint from Fe-coated devices. The Mn-coated devices may also potentially react and be reduced and stripped more rapidly than Fe-coated tubes under comparable conditions.

All identified publications and references are herein incorporated by reference to the same extent as if each individual publication was specifically and individually indicated to be incorporated by reference in its entirety. While the invention has been described in connection with exemplary embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the features hereinbefore set forth.

What is claimed is:

1. A method of producing a manganese oxide coating, comprising:

reducing a potassium permanganate ($KMnO_4$) solution using sodium (Na) lactate, wherein Na lactate:$KMnO_4$ molar ratio is greater than about 6.0;

removing excess Na lactate after said reducing step via one or more washing cycles; and dialyzing said $KMnO_4$ solution for at least 3 days after said step of removing excess Na lactate.

2. The method of claim 1, wherein said manganese oxide coating is stored in a water suspension.

3. The method of claim 1, which said reducing comprises a reaction time of less than 120 minutes.

4. The method of claim 3, wherein said reducing comprises a reaction time of about 10 minutes to about 120 minutes.

\* \* \* \* \*